US011350614B2

(12) United States Patent
Shen et al.

(10) Patent No.: US 11,350,614 B2
(45) Date of Patent: Jun. 7, 2022

(54) GENETICALLY MODIFIED NON-HUMAN ANIMAL WITH HUMAN OR CHIMERIC CD28

(71) Applicant: Biocytogen Pharmaceuticals (Beijing) Co., Ltd., Beijing (CN)

(72) Inventors: Yuelei Shen, Beijing (CN); Yang Bai, Beijing (CN); Yanan Guo, Beijing (CN); Meiling Zhang, Beijing (CN); Rui Huang, Beijing (CN); Chengzhang Shang, Beijing (CN); Jiawei Yao, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 16/435,441

(22) Filed: Jun. 7, 2019

(65) Prior Publication Data

US 2019/0335728 A1    Nov. 7, 2019

Related U.S. Application Data

(63) Continuation of application No. PCT/CN2018/091846, filed on Jun. 19, 2018.

(30) Foreign Application Priority Data

Jun. 19, 2017  (CN) .......................... 201710465217.3
Jun. 15, 2018  (CN) .......................... 201810621710.4

(51) Int. Cl.
*A01K 67/027*  (2006.01)
*A61K 49/00*  (2006.01)
*C07K 14/705*  (2006.01)
*C12N 15/85*  (2006.01)

(52) U.S. Cl.
CPC ...... *A01K 67/0278* (2013.01); *A01K 67/0276* (2013.01); *A61K 49/0008* (2013.01); *C07K 14/70521* (2013.01); *C12N 15/8509* (2013.01); *A01K 2207/15* (2013.01); *A01K 2217/072* (2013.01); *A01K 2217/075* (2013.01); *A01K 2227/105* (2013.01); *A01K 2267/0331* (2013.01); *C07K 2319/03* (2013.01)

(58) Field of Classification Search
CPC .. A01K 67/0275–0278; A01K 2207/15; A01K 2217/072
See application file for complete search history.

(56) References Cited

U.S. PATENT DOCUMENTS

| 4,683,195 A | 7/1987 | Mullis et al. |
| 2002/0115209 A1 | 8/2002 | Liu et al. |
| 2015/0106961 A1 | 4/2015 | Rojas et al. |

FOREIGN PATENT DOCUMENTS

| CN | 101333516 | 12/2008 |
| CN | 103548775 | 2/2014 |
| CN | 105592695 | 5/2016 |
| CN | 106604635 | 4/2017 |
| WO | WO 9510628 | 4/1995 |
| WO | WO 2002059263 | 8/2002 |
| WO | WO 03006639 | 1/2003 |
| WO | WO 2004022735 | 3/2004 |
| WO | WO2004022738 | 3/2004 |
| WO | WO2005060739 | 7/2005 |
| WO | WO 2015049517 | 4/2015 |
| WO | WO2018001241 | 1/2018 |
| WO | WO2018041118 | 3/2018 |
| WO | WO2018041119 | 3/2018 |
| WO | WO2018041120 | 3/2018 |
| WO | WO2018041121 | 3/2018 |
| WO | WO2018068756 | 4/2018 |
| WO | WO2018086583 | 5/2018 |
| WO | WO2018086594 | 5/2018 |
| WO | WO2018121787 | 7/2018 |
| WO | WO2018177440 | 10/2018 |
| WO | WO2018177441 | 10/2018 |

OTHER PUBLICATIONS

Printout from https://en.wikipedia.org/wiki/Genetically_modified_animal, printed 2020, pp. 1-23 (Year: 2020).*
Robert and Ohta. Dev. Dyn. 238(6):1249-1270, 2009 (Year: 2009).*
Hammer. Avian Pathol 3(2):65-78, 1974, abstract only (Year: 1974).*
Dolatshad et al. Mammalian Genome 26:598-608, 2015 (Year: 2015).*
Yao et al. (Scientific Reports 4:6926. DOI:10.1038/srep06926. Nov. 2014. pp. 1-8 (Year: 2014).*
Auerbach et al., "Establishment and Chimera Analysis of 129/Sv-Ev- and C57BL/6-Derived Mouse Embiyonic Stem Cell Lines," BioTechniques, 2000, 29:1024-1032.
Clouthier et al., "Costimulation, a surprising connection for immunotherapy," Science, 2017, 355:1373-1374.
Esensten et al., "CD28 costimulation from mechanism to therapy," Immunity, 2016, 44(5):973-988.
Festing et al., "Revise nomenclature for strain 129 mice," Mammalian Genome, 1999, 10:836.
International Search Report and Written Opinion in International Appln. No. PCT/CN2018/091846, dated Sep. 12, 2018, 11 pages.
Ito, M. et al., NOD/SCID/ ycnull mouse: an excellent recipient mouse model for engraftment of human cells, Blood, 2002, 100(9):3175-3182.
Kamphorst et al., "Rescue of exhausted CD8 T cells by PD-1 targeted therapies is CD28-dependent," Science, 2017, 355(6332):1423-1427.
Mirzoeva et al., "Single administration of p2TA (AB103), a CD28 antagonist peptide, prevents inflammatory and thrombotic reactions and protects against gastrointestinal injury in total-body irradiated mice," PloS one, 2014, 9(7):e101161.
Poirier et al., "First-in-human study in healthy subjects with FR 104, a pegylated monoclonal antibody fragment antagonist of CD28," The Journal of Immunology, 2016, 197(12):4593-4602.

(Continued)

*Primary Examiner* — Marcia S Noble
(74) *Attorney, Agent, or Firm* — Fish & Richardson P.C.

(57) ABSTRACT

The present disclosure relates to genetically modified non-human animals that express a human or chimeric (e.g., humanized) CD28, and methods of use thereof.

15 Claims, 10 Drawing Sheets

Specification includes a Sequence Listing.

(56) References Cited

OTHER PUBLICATIONS

Yin et al., "Delivery technologies for genome editing," Nature Reviews Drug Discovery, 2017, 16(6):387-399.
Brehm et al., "Generation of improved humanized mouse models for human infectious diseases," J Immunol Methods, Aug. 2014, 410:3-17.
Dahan et al., "Therapeutic Activity of Agonistic, Human Anti-CD40 Monoclonal Antibodies Requires Selective FcγR Engagement," Cancer Cell, Jun. 2016, 29(6):820-831.
Li Jiatao, "Human CD137 and CD28 protein expression and monoclonal antibody preparation," Beijing Institute of Tuberculosis and Thoracic Tumor, 2013, 21-38 (with English abstract).
Prasad et al., "T-cell antigen CD28 interacts with the lipid kinase phosphatidylinositol 3-kinase by a cytoplasmic Tyr (P)-Met-Xaa-Met motif," Proceedings of the National Academy of Sciences, Mar. 29, 1994, 91(7):2834-2838.
PCT International Preliminary Report on Patentability in International Appln. No. PCT/CN2018/091846, dated Jan. 2, 2020, 6pages.

* cited by examiner

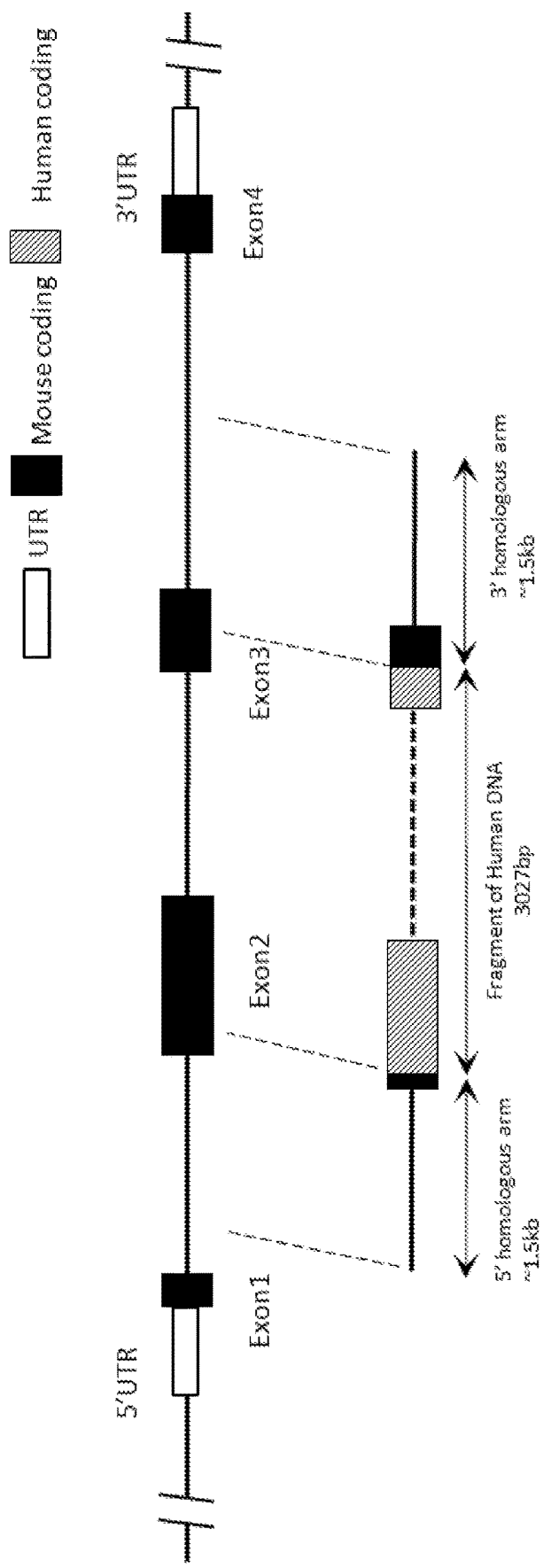
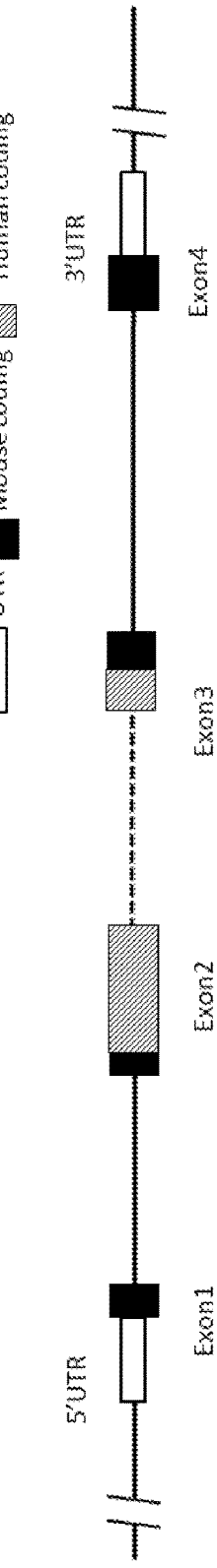
FIG.3
FIG.4

FIG. 11

| Score | Expect | Method | Identities | Positives | Gaps |
|---|---|---|---|---|---|
| 277 bits(709) | 3e-100 | Compositional matrix adjust. | 144/209(69%) | 163/209(77%) | 3/209(1%) |

```
Mouse    12  FFSVQVTENKILLVKQSPLLVVDSNEVSLSCRYSYNLLAKEFRASLYKGVNSDVEVCVGNG   71
                F S+QVT NKILVKQSF+LV    N V+LSC+YSYNL ++EFRASL+KG++S VEVCV  G
Human    11  FPSIQVTGNKILVKQSPMLVAYDNAVNLSCKYSYNLFSREFRASLHKGLDSAVEVCVVYG   70

Mouse    72  NFTYQPQFRSNAEFNCDGDFDNETVTFRLWNLHVNHTDIYFCKIETMYPPPYLDNERSNG  131
                N++ Q Q  S    FNCDG   NE+VTF L NL+VN TDIYFCKIE MYPPPYLDNE+SNG
Human    71  NYSQQLQVYSKTGFNCDGKLGNESVTFYLQNLYVNQTDIYFCKIEVMYPPPYLDNEKSNG  130

Mouse   132  TIIHIKEKHLCHTQSSP----KLFWALVVVAGVLFECYGLLIVTVALCVIWTNSRRNRLLQSD  188
                TIIH+K KHLC +      P    K FW LVVV GVL CY LLVTVA   + W S+R+RLL SD
Human   131  TIIHVKGKHLCPSPLFPGPSKPFWVLVVVGGVLACYSLLIVTVAFIIFWVRSKRSRLLHSD  190

Mouse   189  YMNMTPRRPGLTRKPYQPYAPARDFAAYR  217
                YMNMTPRRPG TRK YQPYAP RDFAAYR
Human   191  YMNMTPRRPGPTRKHYQPYAPPRDFAAYR  219
```

GENETICALLY MODIFIED NON-HUMAN ANIMAL WITH HUMAN OR CHIMERIC CD28

CLAIM OF PRIORITY

This application is a continuation of and claims priority to international Application No. PCT/CN2018/091846, filed on Jun. 19, 2018, which claims the benefit of Chinese Patent Application App. No. 201710465217.3, filed on Jun. 19, 2017, and Chinese Patent Application App. No. 201810621710.4, filed on Jun. 15, 2018. The entire contents of the foregoing are incorporated herein by reference.

TECHNICAL FIELD

This disclosure relates to genetically modified animal expressing human or chimeric (e.g., humanized) CD28, and methods of use thereof.

BACKGROUND

The immune system has developed multiple mechanisms to prevent deleterious activation of immune cells. One such mechanism is the intricate balance between positive and negative costimulatory signals delivered to immune cells. Targeting the stimulatory or inhibitory pathways for the immune system is considered to be a potential approach for the treatment of various diseases, e.g., cancers and autoimmune diseases.

The traditional drug research and development for these stimulatory or inhibitory receptors typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not reflect the real disease state and the interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the cost for drug research and development.

SUMMARY

This disclosure is related to an animal model with human CD28 or chimeric CD28. The animal model can express human CD28 or chimeric CD28 (e.g., humanized CD28) protein in its body. It can be used in the studies on the function of CD28 gene, and can be used in the screening and evaluation of anti-human CD28 antibodies. In addition, the animal models prepared by the methods described herein can be used in drug screening, pharmacodynamics studies, treatments for immune-related diseases (e.g., autoimmune disease), and cancer therapy for human CD28 target sites; they can also be used to facilitate the development and design of new drugs, and save time and cost. In summary, this disclosure provides a powerful tool for studying the function of CD28 protein and a platform for screening cancer drugs.

In one aspect, the disclosure relates to genetically-modified, non-human animals whose genome comprises at least one chromosome comprising a sequence encoding a human or chimeric CD28. In some embodiments, the sequence encoding the human or chimeric CD28 is operably linked to an endogenous regulatory element at the endogenous CD28 gene locus in the at least one chromosome. In some embodiments, the sequence encoding a human or chimeric CD28 comprises a sequence encoding an amino acid sequence that is at least 50%, 55%, 65%, 70%, 75%, 80%, 85%, 90%, 95%, 99%, or 100% identical to human CD28 (NP_006130.1 (SEQ ID NO: 29)). In some embodiments, the sequence encoding a human or chimeric CD28 comprises a sequence encoding an amino acid sequence that is at least 50%, 55%, 65%, 70%, 75%, 80%, 85%, 90%, 95%, 99%, or 100% identical to SEQ ID NO: 33. In some embodiments, the sequence encoding a human or chimeric CD28 comprises a sequence encoding an amino acid sequence that corresponds to amino acids 28-150 of SEQ ID NO: 29.

In some embodiments, the animal is a mammal, e.g., a monkey, a rodent or a mouse. In some embodiments, the animal is a C57BL/6 mouse. In some embodiments, the animal does not express endogenous CD28. In some embodiments, the animal has one or more cells expressing human or chimeric CD28. In some embodiments, the expressed human or chimeric CD28 can bind to or interact with human protein CD80 or CD86. In some embodiments, the expressed human or chimeric CD28 can bind to or interact with endogenous CD80 or CD86.

In one aspect, the disclosure relates to genetically-modified, non-human animals, wherein the genome of the animals comprises a replacement, at an endogenous CD28 gene locus, of a sequence encoding a region of endogenous CD28 with a sequence encoding a corresponding region of human CD28. In some embodiments, the sequence encoding the corresponding region of human CD28 is operably linked to an endogenous regulatory element at the endogenous CD28 locus, and one or more cells of the animal expresses a chimeric CD28. In some embodiments, the animal does not express endogenous CD28. In some embodiments, the locus of endogenous CD28 is the extracellular region of CD28. In some embodiments, the animal has one or more cells expressing a chimeric CD28 having an extracellular region, a transmembrane region, and a cytoplasmic region, wherein the extracellular region comprises a sequence that is at least 50%, 60%, 70%, 80%, 90%, 95%, or 99% identical to the extracellular region of human CD28. In some embodiments, the extracellular region of the chimeric CD28 has a sequence that has at least 10, 20, 30, 40, 50, 60, 70, 80, 90, 100, 110, 120, 130, 140, 150, 160, 170, or 180 contiguous amino acids that are identical to a contiguous sequence present in the extracellular region of human CD28. In some embodiments, the animal is a mouse, and the sequence encoding the region of endogenous CD28 is exon 2 and/or exon 3 of the endogenous mouse CD28 gene. In some embodiments, the animal is heterozygous with respect to the replacement at the endogenous CD28 gene locus. In some embodiments, the animal is homozygous with respect to the replacement at the endogenous CD28 gene locus.

In one aspect, the disclosure relates to methods for making a genetically-modified, non-human animal. The methods involve replacing in at least one cell of the animal, at an endogenous CD28 gene locus, a sequence encoding a region of an endogenous CD28 with a sequence encoding a corresponding region of human CD28. In some embodiments, the sequence encoding the corresponding region of human CD28 comprises exon 1, exon 2, exon 3, and/or exon 4 of a human CD28 gene. In some embodiments, the sequence encoding the corresponding region of CD28 comprises exon 2 and/or exon 3 (or part thereof, e.g., part of exon 2 and/or part of exon 3) of a human CD28 gene. In some embodiments, the sequence encoding the corresponding region of human CD28 encodes amino acids 28-150 of SEQ ID NO: 29. In some embodiments, the region is located within the extracellular region of CD28. In some embodiments, the animal is a mouse, and the sequence encoding the region of the endogenous CD28 locus is exon 1, exon 2, exon 3, and/or exon 4 of mouse CD28 gene (e.g., part of exon 2, part of exon 3).

In one aspect, the disclosure relates to non-human animals comprising at least one cell comprising a nucleotide sequence encoding a chimeric CD28 polypeptide, wherein the chimeric CD28 polypeptide comprises at least 50 contiguous amino acid residues that are identical to the corresponding contiguous amino acid sequence of a human CD28, wherein the animal expresses the chimeric CD28. In some embodiments, the chimeric CD28 polypeptide has at least 50 contiguous amino acid residues that are identical to the corresponding contiguous amino acid sequence of a human CD28 extracellular region. In some embodiments, the chimeric CD28 polypeptide comprises a sequence that is at least 90%, 95%, or 99% identical to amino acids 28-150 of SEQ ID NO: 29. In some embodiments, the nucleotide sequence is operably linked to an endogenous CD28 regulatory element of the animal. In some embodiments, the chimeric CD28 polypeptide comprises an endogenous CD28 transmembrane region and/or an endogenous CD28 cytoplasmic region. In some embodiments, the nucleotide sequence is integrated to an endogenous CD28 gene locus of the animal. In some embodiments, the chimeric CD28 has at least one mouse CD28 activity (e.g., interacting with mouse CD80 or CD86, and promoting immune responses in mice) and/or at least one human CD28 activity (e.g., interacting with human CD80 or CD86, and promoting immune responses in human).

In one aspect, the disclosure relates to methods of making a genetically-modified mouse cell that expresses a chimeric CD28, the method including: replacing, at an endogenous mouse CD28 gene locus, a nucleotide sequence encoding a region of mouse CD28 with a nucleotide sequence encoding a corresponding region of human CD28, thereby generating a genetically-modified mouse cell that includes a nucleotide sequence that encodes the chimeric CD28, wherein the mouse cell expresses the chimeric CD28. In some embodiments, the chimeric CD28 comprises a signal peptide sequence (e.g., a mouse signal peptide sequence or a human signal peptide sequence), an extracellular region of mouse CD28, an extracellular region of human CD28, a transmembrane and/or a cytoplasmic region of a mouse CD28. In some embodiments, the nucleotide sequence encoding the chimeric CD28 is operably linked to an endogenous CD28 regulatory region, e.g., promoter.

In some embodiments, the animals further comprise a sequence encoding an additional human or chimeric protein. In some embodiments, the additional human or chimeric protein is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD40, CD47, CD137, CD154, T-Cell Immunoreceptor With Ig And ITIM Domains (TIGIT), Glucocorticoid-Induced TNFR-Related Protein (GITR), T-cell immunoglobulin and mucin-domain containing-3 (TIM-3), Signal regulatory protein α (SIRPα), or TNF Receptor Superfamily Member 4 (TNFRSF4 or OX40).

In one aspect, the disclosure relates to methods of determining effectiveness of an anti-CD28 antibody for the treatment of cancer, including: administering the anti-CD28 antibody to the animal as described herein, wherein the animal has a tumor, and determining the inhibitory effects of the anti-CD28 antibody to the tumor. In some embodiments, the animal has one or more cells (e.g., T cells, CD4+T cells, CD8+T cells) that express CD28. In some embodiments, the animal has one or more plasma cells that express CD28.

In some embodiments, the tumor comprises one or more cancer cells that are injected into the animal. In some embodiments, determining the inhibitory effects of the anti-CD28 antibody to the tumor involves measuring the tumor volume in the animal. In some embodiments, the tumor cells are melanoma cells (e.g., advanced melanoma cells), non-small cell lung carcinoma (NSCLC) cells, small cell lung cancer (SCLC) cells, bladder cancer cells, non-Hodgkin lymphoma cells, and/or prostate cancer cells (e.g., metastatic hormone-refractory prostate cancer). In some embodiments, the tumor cells are hepatocellular, ovarian, colon, or cervical tumor cells. In some embodiments, the tumor cells are breast cancer cells, ovarian cancer cells, and/or solid tumor cells. In some embodiments, the tumor cells are lymphoma cells, colorectal cancer cells, or oropharyngeal cancer cells. In some embodiments, the animal has metastatic solid tumors, NSCLC, melanoma, lymphoma (e.g., non-Hodgkin lymphoma), colorectal cancer, lung cancer, or multiple myeloma. In some embodiments, the animal has melanoma, pancreatic carcinoma, mesothelioma, hematological malignancies (e.g., Non-Hodgkin's lymphoma, lymphoma, chronic lymphocytic leukemia), or solid tumors.

In one aspect, the disclosure relates to methods of determining effectiveness of an anti-CD28 antibody for the treatment of various immune-related disorders, e.g., autoimmune diseases, multiple sclerosis, rheumatoid arthritis, and psoriasis. In one aspect, the disclosure relates to methods of determining effectiveness of an anti-CD28 antibody for inhibiting transplantation rejection (e.g., allograft rejection).

In one aspect, the disclosure relates to methods of determining effectiveness of an anti-CD28 antibody and an additional therapeutic agent for the treatment of a tumor, including administering the anti-CD28 antibody and the additional therapeutic agent to the animal as described herein, wherein the animal has a tumor, and determining the inhibitory effects on the tumor. In some embodiments, the animal or mouse further comprises a sequence encoding an additional human or chimeric protein. In some embodiments, the additional human or chimeric protein is PD-1, CTLA-4, LAG-3, BTLA, PD-L1, CD27, CD40, CD47, CD137, CD154, TIGIT, TIM-3, GITR, SIRPα, or OX40. In some embodiments, the animal further comprises a sequence encoding a human or chimeric PD-1, PD-L1, or CTLA-4.

In some embodiments, the additional therapeutic agent is an antibody (e.g., human antibody) the specifically binds to PD-1, CTLA-4, LAG-3, BTLA, PD-L1, CD27, CD40, CD47, CD137, CD154, TIGIT, TIM-3, GITR, SIRPα, OX40, CD20, EGFR, or CD319. In some embodiments, the additional therapeutic agent is an anti-PD-1 antibody (e.g., nivolumab), an anti-PD-L1 antibody, an anti-CTLA4 antibody (e.g., ipilimumab), an anti-CD20 antibody (e.g., rituximab), an anti-EGFR antibody (e.g., cetuximab), or an anti-CD319 antibody (e.g., elotuzumab).

In some embodiments, the animal comprises one or more cells (e.g., T cells, CD4+ T cells, CD8+ T cells, plasma cells, B cells) that express CD28. In some embodiments, the animal comprises one or more cells (e.g., antigen presenting cells) that express CD80 or CD86. In some embodiments, the tumor comprises one or more tumor cells that express PD-L1, PD-L2, CD80 or CD86. In some embodiments, the tumor is caused by injection of one or more cancer cells into the animal. In some embodiments, determining the inhibitory effects of the treatment involves measuring the tumor volume in the animal. In some embodiments, the tumor comprises melanoma cells, non-small cell lung carcinoma (NSCLC) cells, small cell lung cancer (SCLC) cells, bladder cancer cells, and/or prostate cancer cells (e.g., metastatic hormone-refractory prostate cancer cells). In some embodiments, the animal has metastatic solid tumors, NSCLC, melanoma, lymphoma (e.g., non-Hodgkin lymphoma), colorectal cancer, or multiple myeloma. In some embodiments, the animal has melanoma, pancreatic carcinoma, mesothelioma, hematological malignancies (e.g., Non-Hodgkin's lymphoma, lymphoma, chronic lymphocytic leukemia), or solid tumors.

In one aspect, the disclosure relates to proteins comprising an amino acid sequence, wherein the amino acid sequence is one of the following: (a) an amino acid sequence set forth in SEQ ID NO: 33; (b) an amino acid sequence that is at least 90% identical to SEQ ID NO: 33; (c) an amino acid sequence that is at least 91%, 92%, 93%, 94%, 95%, 96%, 97%, 98%, or 99% identical to SEQ ID NO: 33; (d) an amino acid sequence that is different from the amino acid sequence set forth in SEQ ID NO: 33 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 33. In some embodiments, provided herein are cells comprising the proteins disclosed herein. In some embodiments, provided herein are animals having the proteins disclosed herein.

In one aspect, the disclosure relates to nucleic acids comprising a nucleotide sequence, wherein the nucleotide sequence is one of the following: (a) a sequence that encodes the protein as described herein; (b) SEQ ID NO: 31; (c) SEQ ID NO: 32; (d) a sequence that is at least 90% identical to SEQ ID NO: 31 or SEQ ID NO: 32; (e) a sequence that is at least 91%, 92%, 93%, 94%, 95%, 96%, 97%, 98%, or 99% identical to SEQ ID NO: 31; and (f) a sequence that is at least 91%, 92%, 93%, 94%, 95%, 96%, 97%, 98%, or 99% identical to SEQ ID NO: 32. In some embodiments, provided herein are cells comprising the nucleic acids disclosed herein. In some embodiments, provided herein are animals having the nucleic acids disclosed herein.

In another aspect, the disclosure also provides a genetically-modified, non-human animal whose genome comprise a disruption in the animal's endogenous CD28 gene, wherein the disruption of the endogenous CD28 gene comprises deletion of exon 1, exon 2, exon 3, and/or exon 4, or part thereof of the endogenous CD28 gene.

In some embodiments, the disruption of the endogenous CD28 gene comprises deletion of one or more exons or part of exons selected from the group consisting of exon 1, exon 2, exon 3, and exon 4 of the endogenous CD28 gene.

In some embodiments, the disruption of the endogenous CD28 gene further comprises deletion of one or more introns or part of introns selected from the group consisting of intron 1, intron 2, and intron 3 of the endogenous CD28 gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, or more nucleotides.

In some embodiments, the disruption of the endogenous CD28 gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, or 300 nucleotides of exon 1, exon 2, exon 3, and/or exon 4 (e.g., deletion of at least 300 nucleotides of exon 2 and/or deletion of at least 100 nucleotides of exon 3).

In some embodiments, the mice described in the present disclosure can be mated with the mice containing other human or chimeric genes (e.g., chimeric SIRPα, chimeric PD-1, chimeric PD-L1, chimeric CTLA-4, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy.

In another aspect, the disclosure further provides methods of determining toxicity of an agent (e.g., a CD28 antagonist or agonist). The methods involve administering the agent to the animal as described herein; and determining weight change of the animal. In some embodiments, the methods further involve performing a blood test (e.g., determining red blood cell count).

In one aspect, the disclosure relates to a targeting vector, including a) a DNA fragment homologous to the 5' end of a region to be altered (5' arm), which is selected from the CD28 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CD28 gene genomic DNAs in the length of 100 to 10,000 nucleotides.

In some embodiments, a) the DNA fragment homologous to the 5' end of a region to be altered (5' arm/receptor) is selected from the nucleotide sequences that have at least 90% homology to the NCBI accession number NC_000067.6; c) the DNA fragment homologous to the 3' end of the region to be altered (3' arm/receptor) is selected from the nucleotide sequences that have at least 90% homology to the NCBI accession number NC_000067.6.

In some embodiments, a) the DNA fragment homologous to the 5' end of a region to be altered (5' arm/receptor) is selected from the nucleotides from the position 60761678 to the position 60763007 of the NCBI accession number NC_000067.6; c) the DNA fragment homologous to the 3' end of the region to be altered (3' arm/receptor) is selected from the nucleotides from the position 60765309 to the position 60766648 of the NCBI accession number NC_000067.6.

In some embodiments, a length of the selected genomic nucleotide sequence is more than 2 kb, 2.5 kb, 3 kb, 3.5 kb, or 4 kb. In some embodiments, the length is about 3027 bp. In some embodiments, the region to be altered is exon 2, and/or exon 3 of mouse CD28 gene.

In some embodiments, the sequence of the 5' arm is shown in SEQ ID NO: 34. In some embodiments, the sequence of the 3' arm is shown in SEQ ID NO: 36.

In some embodiments, the targeting vector further includes a selectable gene marker.

In some embodiments, the target region is derived from human. In some embodiments, the target region is a part or entirety of the nucleotide sequence of the human CD28. In some embodiments, the nucleotide sequence is shown as one or more of exon 1, exon 2, exon 3, and exon 4 of the human CD28.

In some embodiments, the nucleotide sequence of the human CD28 encodes the human CD28 protein with the NCBI accession number NP_006130.1 (SEQ ID NO: 29). In some emboldens, the nucleotide sequence of the human CD28 is selected from the nucleotides from the position 203726662 to the position 203729688 of NC_000002.12 (SEQ ID NO: 35).

The disclosure also relates to a cell including the targeting vector as described herein.

The disclosure also relates to a method for establishing a genetically-modified non-human animal expressing two human or chimeric (e.g., humanized) genes. The method includes the steps of (a) using the method for establishing a CD28 gene humanized animal model to obtain a CD28 gene genetically modified humanized mouse;

(b) mating the CD28 gene genetically modified humanized mouse obtained in step (a) with another humanized mouse, and then screening to obtain a double humanized mouse model.

In some embodiments, in step (b), the CD28 gene genetically modified humanized mouse obtained in step (a) is mated with a PD-1 or PD-L1 humanized mouse to obtain a CD28 and PD-1 double humanized mouse model or a CD28 and PD-L1 double humanized mouse model.

The disclosure also relates to a non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized CD28 gene.

The disclosure also relates to an offspring of the non-human mammal.

In another aspect, the disclosure relates to a tumor bearing non-human mammal model, characterized in that the non-human mammal model is obtained through the methods as described herein.

In some embodiments, the non-human mammal is a rodent. In some embodiments, the non-human mammal is a mouse.

The disclosure also relates to a cell (e.g., stem cell or embryonic stem cell) or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a CD28 amino acid sequence of a humanized mouse, wherein the amino acid sequence is selected from the group consisting of:

a) an amino acid sequence shown in SEQ ID NO: 33;

b) an amino acid sequence having a homology of at least 90% with the amino acid sequence shown in SEQ ID NO: 33;

c) an amino acid sequence encoded by a nucleic acid sequence, wherein the nucleic acid sequence is able to hybridize to a nucleotide sequence encoding the amino acid shown in SEQ ID NO: 33 under a low stringency condition or a strict stringency condition;

d) an amino acid sequence having a homology of at least 90%, 91%, 92%, 93%, 94%, 95%, 96%, 97%, 98%, or at least 99% with the amino acid sequence shown in SEQ ID NO: 33;

e) an amino acid sequence that is different from the amino acid sequence shown in SEQ ID NO: 33 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 33.

The disclosure also relates to a CD28 nucleic acid sequence of a humanized mouse, wherein the nucleic acid sequence is selected from the group consisting of:

a) a nucleic acid sequence that encodes the CD28 amino acid sequence of a humanized mouse;

b) a nucleic acid sequence that is set forth in SEQ ID NO: 31 or SEQ ID NO: 32;

c) a nucleic acid sequence that can hybridize to the nucleotide sequence as shown in SEQ ID NO: 31 or SEQ ID NO: 32 under a low stringency condition or a strict stringency condition;

d) a nucleic acid sequence that has a homology of at least 90%, 91%, 92%, 93%, 94%, 95%, 96%, 97%, 98%, or at least 99% with the nucleotide sequence as shown in SEQ ID NO: 31 or SEQ ID NO: 32;

f) a nucleic acid sequence that encodes an amino acid sequence, wherein the amino acid sequence has a homology of at least 90% with the amino acid sequence shown in SEQ ID NO: 33;

g) a nucleic acid sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 33;

h) a nucleic acid sequence that encodes an amino acid sequence, wherein the amino acid sequence is different from the amino acid sequence shown in SEQ ID NO: 33 by no more than 10, 9, 8, 7, 6, 5, 4, 3, 2 or no more than 1 amino acid; and/or i) a nucleic acid sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 33.

The disclosure further relates to a CD28 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the CD28 gene function, human CD28 antibodies, the drugs or efficacies for human CD28 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 3 is a schematic diagram showing a gene targeting strategy.

FIG. 4 is a schematic diagram showing a map of an example of humanized CD28 gene in mouse.

FIG. 11 shows the alignment between mouse CD28 amino acid sequence (NP_031668.3; SEQ ID NO: 27) and human CD28 amino acid sequence (NP_006130.1; SEQ ID NO: 29).

DETAILED DESCRIPTION

Figures 1A, 1B:
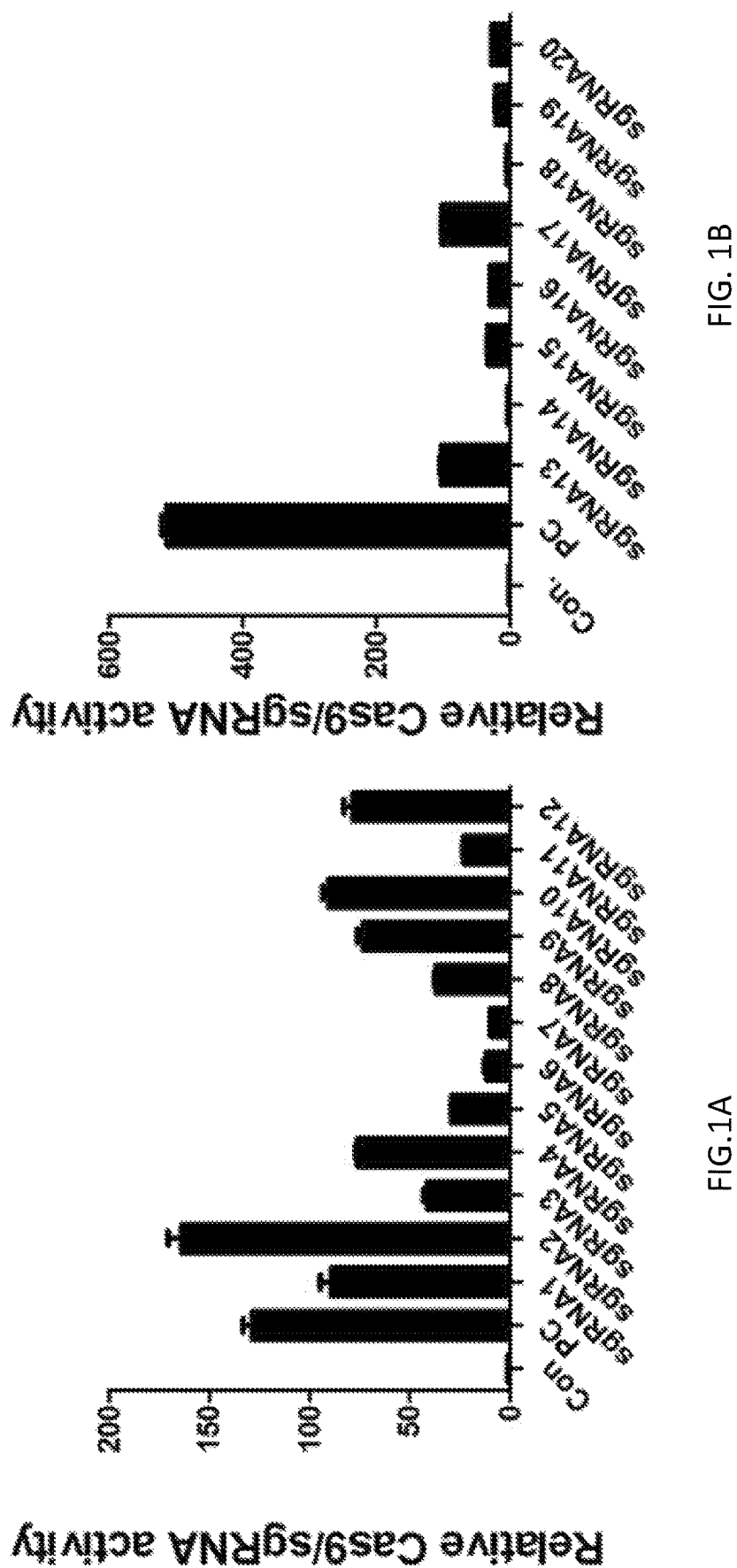
FIG. 1A is a graph showing activity testing results for sgRNA1-sgRNA12 (Con is a negative control; PC is a positive control).
FIG. 1B is a graph showing activity testing results for sgRNA13-sgRNA20 (Con is a negative control; PC is a positive control).

This disclosure relates to transgenic non-human animal with human or chimeric (e.g., humanized) CD28, and methods of use thereof.

CD28 is one of the proteins expressed on T cells that provide co-stimulatory signals required for T cell activation and survival. T cell stimulation through CD28 in addition to the T-cell receptor (TCR) can provide a potent signal for the production of various interleukins (e.g., IL-6, IL-13).

CD28 are mainly expressed on T cells, and its expression increases after T cell activation. CD28 interacts with molecules of the B7 family present mainly at the surface of murine and human APCs, as well as on activated T and B cells. CD28 is the receptor for CD80 (B7-1) and CD86 (B7-2) proteins. After engagement of the TCR with a class II (or I) MHC molecule on the APC, IL-2 production and IL-2 receptor expression are initiated; the second signal provided by the CD28/CD80 or CD28/CD86 interaction stabilizes IL-2 mRNA and increases IL-2 secretion, resulting in T cell proliferation and clonal expansion, thereby promoting immune response. Thus, CD28 antibodies can be potentially used to treat cancers or autoimmune diseases.

Experimental animal models are an indispensable research tool for studying the effects of these antibodies (e.g., CD28 antibodies). Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullisetal U.S. Pat. No. 4,683,195; Nucleic Acid Hybridization (B. D. Hames & S. J. Higginseds. 1984); Transcription And Translation (B. D. Hames & S. J. Higginseds 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wuetal. eds.) and Vol. 185, "Gene Expression Technology" (D. Goeddel, ed.); Gene Transfer Vectors For Mammalian Cells (J. H. Miller and M. P. Calloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986); each of which is incorporated herein by reference in its entirety.

CD28

CD28 is a member of a subfamily of costimulatory molecules characterized by an extracellular variable immunoglobulin-like domain. Other members of the subfamily include ICOS, CTLA4, PD1, PD1H, and BTLA. CD28 is expressed constitutively on mouse T cells, whereas the expression of other family members ICOS and CTLA4 is induced by T cell receptor stimulation and in response to cytokines such as interleukin 2 (IL-2). CD28 is expressed on roughly 80% of human CD4+ T cells and 50% CD8+ T cells.

The CD28 ligands CD80 and CD86 diverge in their expression patterns, multimeric states, and functionality, adding another layer of complexity to the regulation of CD28 signaling. CD80 is present in predominantly dimeric form on the cell surface whereas CD86 is monomeric. CD86 is expressed constitutively on antigen presenting cells (APCs) and is rapidly upregulated by innate stimuli of APCs, whereas the other CD28 ligand, CD80, is upregulated at later time points. CD86 may therefore be more important in the initiation of immune responses. CD80 and CD86 are induced by different stimuli in different cell types and they are usually not interchangeable in function.

CD28 and CTLA4 are highly homologous and compete for the same ligands (B7-1 (CD80) and B7-2 (CD86)). CTLA4 binds these ligands with a higher affinity than CD28, which allows CTLA4 to compete with CD28 for ligand and suppress effector T cells responses. CD28 and CTLA4 have opposing effects on T cell stimulation. CD28 provides an activating signal and CTLA4 provides an inhibitory signal, which is now considered a prototypical immune checkpoint. Although CTLA4 binding to CD80 or CD86 is always stronger than CD28 binding, when in competition, CD86 has a relative preference for CD28 compared to CD80, which binds very strongly to CTLA4. Thus, the sequential expression CD86 followed by CD80 on APCs may function to increase the suppressive function of CTLA4 once an immune response has started, since the CTLA4-CD80 interaction later in an immune response is particularly strong. Recent research also showed that CD28/B7 costimulatory pathway is essential for effective PD-1 therapy for treating chronic viral infection and tumor in mice.

In addition to T cells, plasma cells also express CD28. CD28 signals may regulate antibody production by plasma cells or plasma cell survival although the precise role that CD28 plays in plasma cell biology is still unclear.

Furthermore, based on the opposing effects of engagement of CD28 and CTLA-4 by B7 family ligands on adaptive immunity, blocking the CD28:CD80/CD86 (CD28: B7) costimulatory pathway by selectively targeting CD28 instead of B7 can be highly effective to modulate pathogenic T cell responses. Non-activating antagonist monovalent Ab fragments against CD28 can prevent allograft rejection in mice as well as in non-human primates. Besides transplantation, preclinical proofs of concept have also been obtained in using anti-CD28 antibodies for treating multiple sclerosis, rheumatoid arthritis, and psoriasis.

A detailed description of CD28 and its function can be found, e.g., in Esensten, et al. "CD28 costimulation: from mechanism to therapy." Immunity 44.5 (2016): 973-988; Kamphorst, et al. "Rescue of exhausted CD8 T cells by PD-1-targeted therapies is CD28-dependent." Science 355.6332 (2017): 1423-1427; Mirzoeva, et al. "Single administration of p2TA (AB103), a CD28 antagonist peptide, prevents inflammatory and thrombotic reactions and protects against gastrointestinal injury in total-body irradiated mice." PloS one 9.7 (2014): e101161; Poirier et al. "First-in-human study in healthy subjects with FR104, a pegylated monoclonal antibody fragment antagonist of CD28." The Journal of Immunology 197.12 (2016): 4593-4602; each of which is incorporated by reference in its entirety.

In human genomes, CD28 gene (Gene ID: 940) locus has four exons, exon 1, exon 2, exon 3, and exon 4. The CD28 protein also has an extracellular region, a transmembrane region, and a cytoplasmic region, and the signal peptide is located at the extracellular region of CD28. The nucleotide sequence for human CD28 mRNA is NM_006139.3 (SEQ ID NO: 28), and the amino acid sequence for human CD28 is NP_006130.1 (SEQ ID NO: 29). The location for each exon and each region in human CD28 nucleotide sequence and amino acid sequence is listed below:

TABLE 1

| Human CD28 (approximate location) | NM_006139.3 4900 bp (SEQ ID NO: 28) | NP_006130.1 220 aa (SEQ ID NO: 29) |
|---|---|---|
| Exon 1 | 1-274 | 1-17 |
| Exon 2 | 275-63 | 18-136 |
| Exon 3 | 632-756 | 137-178 |
| Exon 4 | 757-4885 | 179-220 |
| Signal peptide | 223-276 | 1-18 |
| Extracellular region (excluding signal peptide region) | 277-678 | 19-152 |
| Transmembrane region | 679-759 | 153-179 |
| Cytoplasmic region | 760-882 | 180-220 |
| Donor region in Example | 304-672 | 28-150 |

In mice, CD28 gene locus has four exons, exon 1, exon 2, exon 3, and exon 4 (FIG. 3). The mouse CD28 protein also has an extracellular region, a transmembrane region, and a cytoplasmic region, and the signal peptide is located at the extracellular region of CD28. The nucleotide sequence for mouse CD28 cDNA is NM_007642.4 (SEQ ID NO: 26), the amino acid sequence for mouse CD28 is NP_031668.3 (SEQ ID NO: 27). The location for each exon and each region in the mouse CD28 nucleotide sequence and amino acid sequence is listed below:

TABLE 2

| Mouse CD28 (approximate location) | NM_007642.4 4317 bp (SEQ ID NO: 26) | NP_031668.3 218 aa (SEQ ID NO: 27) |
|---|---|---|
| Exon 1 | 1-141 | 1-18 |
| Exon 2 | 142-498 | 19-137 |
| Exon 3 | 499-614 | 138-176 |
| Exon 4 | 615-4317 | 177-218 |
| Signal peptide | 87-143 | 1-19 |
| Extracellular region (excluding signal peptide region) | 144-536 | 20-150 |
| Transmembrane region | 537-617 | 151-177 |
| Cytoplasmic region | 618-740 | 178-218 |
| Replaced region in Example | 171-530 | 29-148 |

The mouse CD28 gene (Gene ID: 12487) is located in Chromosome 1 of the mouse genome, which is located from 60746388 to 60773359 of NC_000067.6 (GRCm38.p4 (GCF_000001635.24)). The 5'-UTR is from 60746388 to 60746473, exon 1 is from 60746358 to 60746528, the first intron is from 60746529 to 60762978, exon 2 is from 60762979 to 60763335, the second intron is from 60763336 to 60765276, exon 3 is from 60765277 to 60765392, the third intron is from 60765393 to 60769656, exon 4 is from 60769657 to 60773359, the 3'-UTR is from 60769786 to 60773359, based on transcript NM_007642.4. All relevant information for mouse CD28 locus can be found in the NCBI website with Gene ID: 12487, which is incorporated by reference herein in its entirety.

FIG. 11 shows the alignment between mouse CD28 amino acid sequence (NP_031668.3; SEQ ID NO: 27) and human CD28 amino acid sequence (NP_006130.1; SEQ ID NO: 29). Thus, the corresponding amino acid residue or region between human and mouse CD28 can be found in FIG. 11.

CD28 genes, proteins, and locus of the other species are also known in the art. For example, the gene ID for CD28 in *Rattus norvegicus* is 25660, the gene ID for CD28 in *Macaca mulatta* (Rhesus monkey) is 705313, the gene ID for CD28 in *Canis lupus* familiaris (dog) is 403646, and the gene ID for CD28 in *Sus scrofa* (pig) is 100515419. The relevant information for these genes (e.g., intron sequences, exon sequences, amino acid residues of these proteins) can be found, e.g., in NCBI database, which is incorporated by reference herein in its entirety.

The present disclosure provides human or chimeric (e.g., humanized) CD28 nucleotide sequence and/or amino acid sequences. In some embodiments, the entire sequence of mouse exon 1, exon 2, exon 3, exon 4, signal peptide, extracellular region, transmembrane region, and/or cytoplasmic region are replaced by the corresponding human sequence. In some embodiments, a "region" or "portion" of mouse exon 1, exon 2, exon 3, exon 4, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 250, 300, 350, 400, 500, or 600 nucleotides, or at least 1, 2, 3, 4, 5, 6, 7, 8, 9, 10, 20, 30, 40, 50, 60, 70, 80, 90, 100, 110, 120, 130, 140, 150, 160, 170, 180, 190, or 200 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, signal peptide, extracellular region, transmembrane region, or cytoplasmic region. In some embodiments, a region, a portion, or the entire sequence of mouse exon 1, exon 2, exon 3, and/or exon 4 (e.g., exon 2, exon 3) are replaced by the human exon 1, exon 2, exon 3, and/or exon 4 (e.g., exon 2, exon 3) sequence.

In some embodiments, the present disclosure also provides a chimeric (e.g., humanized) CD28 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse CD28 mRNA sequence (e.g., SEQ ID NO: 26), mouse CD28 amino acid sequence (e.g., SEQ ID NO: 27), or a portion thereof (e.g., exon 1, exon 2, exon 3, exon 4); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human CD28 mRNA sequence (e.g., SEQ ID NO: 28), human CD28 amino acid sequence (e.g., SEQ ID NO: 29), or a portion thereof (e.g., exon 2, and exon 3).

In some embodiments, the sequence encoding amino acids 29-148 of mouse CD28 (SEQ ID NO: 27) is replaced. In some embodiments, the sequence is replaced by a sequence encoding a corresponding region of human CD28 (e.g., amino acids 28-150 of human CD28 (SEQ ID NO: 29)).

In some embodiments, the nucleic acids as described herein are operably linked to a promotor or regulatory element, e.g., an endogenous mouse CD28 promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse CD28 nucleotide sequence (e.g., exon 2, exon 3, or NM_007642.4 (SEQ ID NO: 26)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse CD28 nucleotide sequence (e.g., exon 2, exon 3, or NM_007642.4 (SEQ ID NO: 26)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human CD28 nucleotide sequence (e.g., exon 2, exon 3, or NM_006139.3 (SEQ ID NO: 28)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human CD28 nucleotide sequence (e.g., exon 2, exon 3, or NM_006139.3 (SEQ ID NO: 28)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse CD28 amino acid sequence (e.g., exon 2, exon 3, or NP_031668.3 (SEQ ID NO: 27)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse CD28 amino acid sequence (e.g., exon 2, exon 3, or NP_031668.3 (SEQ ID NO: 27)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human CD28 amino acid sequence (e.g., exon 2, exon 3, or NP_006130.1 (SEQ ID NO: 29)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human CD28 amino acid sequence (e.g., exon 2, exon 3, or NP_006130.1 (SEQ ID NO: 29)).

The present disclosure also provides a humanized CD28 mouse amino acid sequence, wherein the amino acid sequence is selected from the group consisting of:

a) an amino acid sequence shown in SEQ ID NO: 33;

b) an amino acid sequence having a homology of at least 90% with or at least 90% identical to the amino acid sequence shown in SEQ ID NO: 33;

c) an amino acid sequence encoded by a nucleic acid sequence, wherein the nucleic acid sequence is able to hybridize to a nucleotide sequence encoding the amino acid shown in SEQ ID NO: 33 under a low stringency condition or a strict stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 33;

e) an amino acid sequence that is different from the amino acid sequence shown in SEQ ID NO: 33 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 33.

The present disclosure also relates to a CD28 nucleic acid (e.g., DNA or RNA) sequence, wherein the nucleic acid sequence can be selected from the group consisting of:

a) a nucleic acid sequence as shown in SEQ ID NO: 31, or a nucleic acid sequence encoding a homologous CD28 amino acid sequence of a humanized mouse;

b) a nucleic acid sequence that is shown in SEQ ID NO: 32;

c) a nucleic acid sequence that is able to hybridize to the nucleotide sequence as shown in SEQ ID NO: 31 or SEQ ID NO: 32 under a low stringency condition or a strict stringency condition;

d) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 31 or SEQ ID NO: 32;

e) a nucleic acid sequence that encodes an amino acid sequence, wherein the amino acid sequence has a homology of at least 90% with or at least 90% identical to the amino acid sequence shown in SEQ ID NO: 33;

f) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 33;

g) a nucleic acid sequence that encodes an amino acid sequence, wherein the amino acid sequence is different from the amino acid sequence shown in SEQ ID NO: 33 by no more than 10, 9, 8, 7, 6, 5, 4, 3, 2 or no more than 1 amino acid; and/or h) a nucleic acid sequence that encodes an amino acid sequence, wherein the amino acid sequence comprises a substitution, a deletion and/or insertion of one or more amino acids to the amino acid sequence shown in SEQ ID NO: 33.

The present disclosure further relates to a CD28 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 31 or SEQ ID NO: 32.

The disclosure also provides an amino acid sequence that has a homology of at least 90% with, or at least 90% identical to the sequence shown in SEQ ID NO: 33, and has protein activity. In some embodiments, the homology with the sequence shown in SEQ ID NO: 33 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 33 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 31 or SEQ ID NO: 32, and encodes a polypeptide that has protein activity. In some embodiments, the homology with the sequence shown in SEQ ID NO: 31 or SEQ ID NO: 32 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

In some embodiments, the percentage identity with the sequence shown in SEQ ID NO: 31 or SEQ ID NO: 32 is at least about 90%, 91%, 92%, 93%, 94%, 95%, 96%, 97%, 98%, or at least 99%. In some embodiments, the foregoing percentage identity is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99° A identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity. Families of amino acid residues having similar physicochemical properties have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express human or chimeric (e.g., humanized) CD28 from an endogenous non-human CD28 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, an antigen presenting cell, a macrophage, a dendritic cell, a germ cell, a blastocyst, or an endogenous tumor cell. In some embodiments, genetically-modified non-human animals are provided that comprise a modified endogenous CD28 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized CD28 gene or a humanized CD28 nucleic acid. In some embodiments, at least one or more portions of the gene or the nucleic acid is from the human CD28 gene, at least one or more portions of the gene or the nucleic acid is from a non-human CD28 gene. In some embodiments, the gene or the nucleic acid comprises a sequence that encodes a CD28 protein. The encoded CD28 protein is functional or has at least one activity of the human CD28 protein or the non-human CD28 protein, e.g., binding with human or non-human CD80 or CD86, increasing production of proinflammatory cytokines, inducing activation and proliferation of immune cells (e.g., T cells), increasing the production of cytokines (e.g., IL-2), and/or upregulating the immune response.

In some embodiments, the chimeric protein or the chimeric polypeptide is a humanized CD28 protein or a humanized CD28 polypeptide. In some embodiments, at least one or more portions of the amino acid sequence of the protein or the polypeptide is from a human CD28 protein, and at least one or more portions of the amino acid sequence of the protein or the polypeptide is from a non-human CD28 protein. The humanized CD28 protein or the humanized CD28 polypeptide is functional or has at least one activity of the human CD28 protein or the non-human CD28 protein.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, withtailed rats, Malagasy rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10: 836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized CD28 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100 (9): 3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human CD28 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of a mature CD28 coding sequence with a human mature CD28 coding sequence.

Genetically modified non-human animals that comprise a modification of an endogenous non-human CD28 locus. In some embodiments, the modification can comprise a human nucleic acid sequence encoding at least a portion of a mature CD28 protein (e.g., at least 10%, 20%, 30%, 40%, 50%, 60%, 70%, 80%, 90%, 95%, 96%, 97%, 98%, or 99% identical to the mature CD28 protein sequence). Although genetically modified cells are also provided that can comprise the modifications described herein (e.g., ES cells, somatic cells), in many embodiments, the genetically modified non-human animals comprise the modification of the endogenous CD28 locus in the germline of the animal.

Genetically modified animals can express a human CD28 and/or a chimeric (e.g., humanized) CD28 from endogenous mouse loci, wherein the endogenous mouse CD28 gene has been replaced with a human CD28 gene and/or a nucleotide sequence that encodes a region of human CD28 sequence or an amino acid sequence that is at least 10%, 20%, 30%, 40%, 50%, 60%, 70&, 80%, 90%, 95%, 96%, 97%, 98%, or 99% identical to the human CD28 sequence. In various embodiments, an endogenous non-human CD28 locus is modified in whole or in part to comprise human nucleic acid sequence encoding at least one protein-coding sequence of a mature CD28 protein.

In some embodiments, the genetically modified mice express the human CD28 and/or chimeric CD28 (e.g., humanized CD28) from endogenous loci that are under control of mouse promoters and/or mouse regulatory elements. The replacement(s) at the endogenous mouse loci provide non-human animals that express human CD28 or chimeric CD28 (e.g., humanized CD28) in appropriate cell types and in a manner that does not result in the potential pathologies observed in some other transgenic mice known in the art. The human CD28 or the chimeric CD28 (e.g., humanized CD28) expressed in animal can maintain one or more functions of the wildtype mouse or human CD28 in the animal. For example, human or non-human CD28 ligands (e.g., CD80 or CD86) can bind to the expressed CD28, upregulate immune response, e.g., upregulate immune response by at least 10%, 20%, 30%, 40%, or 50%. Furthermore, in some embodiments, the animal does not express endogenous CD28. As used herein, the term "endogenous CD28" refers to CD28 protein that is expressed from an endogenous CD28 nucleotide sequence of the non-human animal (e.g., mouse) before any genetic modification.

The genome of the animal can comprise a sequence encoding an amino acid sequence that is at least 70%, 75%, 80%, 85%, 90%, 95%, 99%, or 100% identical to human CD28 (NP_006130.1) (SEQ ID NO: 29). In some embodiments, the genome comprises a sequence encoding an amino acid sequence that is at least 70%, 75%, 80%, 85%, 90%, 95%, 99%, or 100% identical to SEQ ID NO: 33.

The genome of the genetically modified animal can comprise a replacement at an endogenous CD28 gene locus of a sequence encoding a region of endogenous CD28 with a sequence encoding a corresponding region of human CD28. In some embodiments, the sequence that is replaced is any sequence within the endogenous CD28 gene locus, e.g., exon 1, exon 2, exon 3, exon 4, 5'-UTR, 3'-UTR, the first intron, the second intron, and the third intron, etc. In some embodiments, the sequence that is replaced is within the regulatory region of the endogenous CD28 gene. In some embodiments, the sequence that is replaced is exon 2, intron 2, exon 3, or part thereof, of an endogenous mouse CD28 gene locus.

The genetically modified animal can have one or more cells expressing a human or chimeric CD28 (e.g., humanized CD28) having an extracellular region and a cytoplasmic region, wherein the extracellular region comprises a sequence that is at least 50%, 60%, 70%, 80%, 90%, 95%, 99% identical to the extracellular region of human CD28. In some embodiments, the extracellular region of the humanized CD28 has a sequence that has at least 10, 20, 30, 40, 50, 60, 70, 80, 90, 100, 110, 120, 130, 140, 150, 160, 170, or 180 amino acids (e.g., contiguously or non-contiguously) that are identical to human CD28. Because human CD28 and non-human CD28 (e.g., mouse CD28) sequences, in many cases, are different, antibodies that bind to human CD28 will not necessarily have the same binding affinity with non-human CD28 or have the same effects to non-human CD28. Therefore, the genetically modified animal having a human or a humanized extracellular region can be used to better evaluate the effects of anti-human CD28 antibodies in an animal model. In some embodiments, the genome of the genetically modified animal comprises a sequence encoding an amino acid sequence that corresponds to part or the entire sequence of exon 2, and/or exon 3 of human CD28, part or the entire sequence of extracellular region of human CD28 (with or without signal peptide), or part or the entire sequence of amino acids 28-150 of SEQ ID NO: 29.

In some embodiments, the non-human animal can have, at an endogenous CD28 gene locus, a nucleotide sequence encoding a chimeric human/non-human CD28 polypeptide, wherein a human portion of the chimeric human/non-human CD28 polypeptide comprises a portion of human CD28 extracellular domain, and wherein the animal expresses a functional CD28 on a surface of a cell of the animal. The human portion of the chimeric human/non-human CD28 polypeptide can comprise a portion of exon 2, and/or exon 3 of human CD28. In some embodiments, the human portion of the chimeric human/non-human CD28 polypeptide can comprise a sequence that is at least 80%, 85%, 90%, 95%, or 99% identical to amino acids 28-150 of SEQ ID NO: 29.

In some embodiments, the non-human portion of the chimeric human/non-human CD28 polypeptide comprises transmembrane and/or cytoplasmic regions of an endogenous non-human CD28 polypeptide. There may be several advantages that are associated with the transmembrane and/or cytoplasmic regions of an endogenous non-human CD28 polypeptide. For example, once a CD28 ligand (e.g., CD80 or CD86) or an anti-CD28 antibody binds to CD28, they can properly transmit extracellular signals into the cells and initiate the downstream pathway. A human or humanized transmembrane and/or cytoplasmic regions may not function properly in non-human animal cells. In some embodiments, a few extracellular amino acids that are close to the transmembrane region of CD28 are also derived from endogenous sequence. These amino acids can also be important for transmembrane signal transmission.

Furthermore, the genetically modified animal can be heterozygous with respect to the replacement at the endogenous CD28 locus, or homozygous with respect to the replacement at the endogenous CD28 locus.

In some embodiments, the humanized CD28 locus lacks a human CD28 5'-UTR. In some embodiment, the humanized CD28 locus comprises a rodent (e.g., mouse) 5'-UTR. In some embodiments, the humanization comprises a human 3'-UTR. In appropriate cases, it may be reasonable to presume that the mouse and human CD28 genes appear to be similarly regulated based on the similarity of their 5'-flanking sequence. As shown in the present disclosure, humanized CD28 mice that comprise a replacement at an endogenous mouse CD28 locus, which retain mouse regulatory elements but comprise a humanization of CD28 encoding sequence, do not exhibit pathologies. Both genetically modified mice that are heterozygous or homozygous for humanized CD28 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized CD28 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized CD28 in the genome of the animal.

Figure 2:
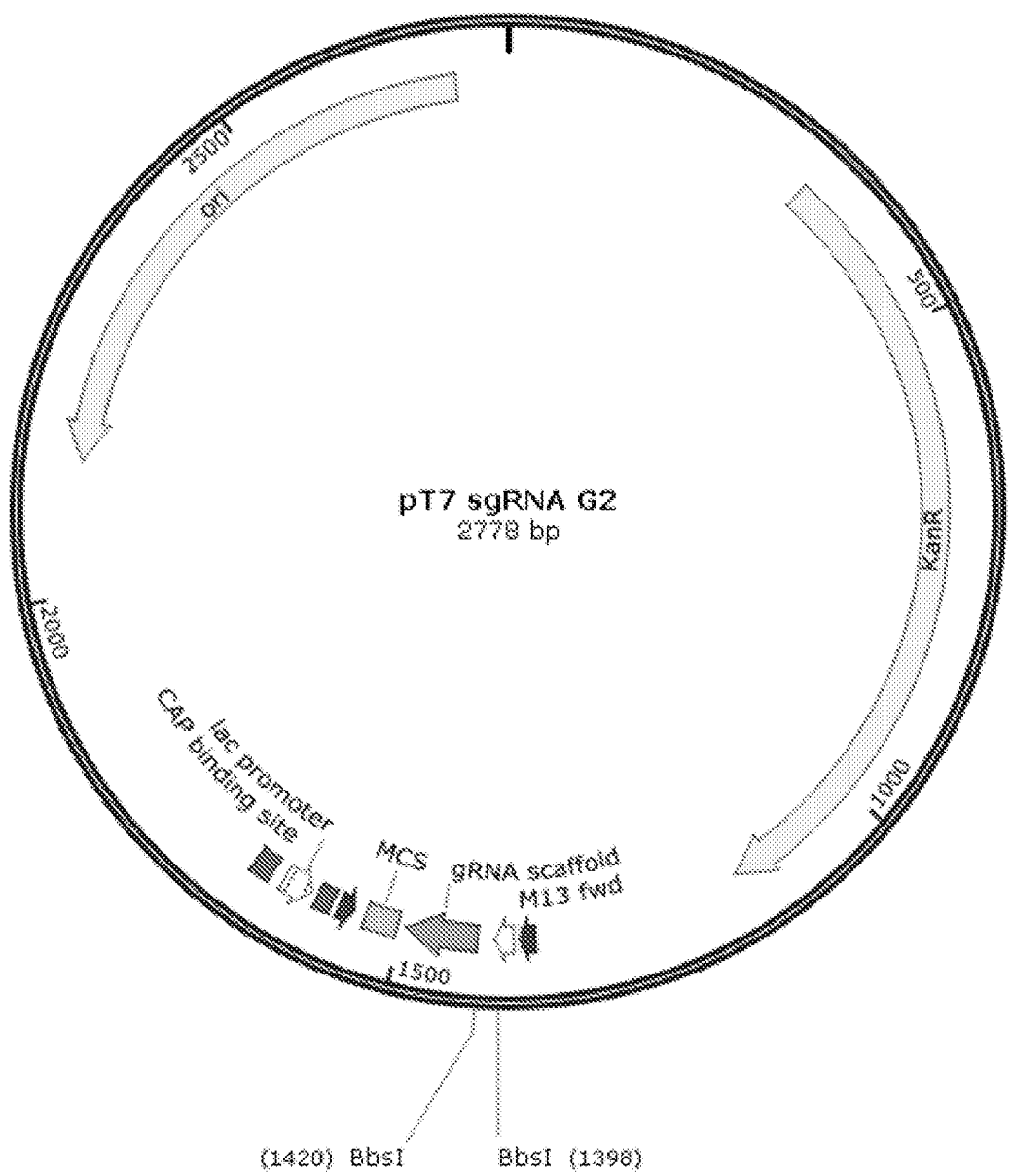
FIG. 2 is a schematic diagram showing the structure of pT7-sgRNA-G2 plasmid.

In some embodiments, the non-human mammal comprises the genetic construct as described herein (e.g., gene construct as shown in FIG. 2 or FIG. 3). In some embodiments, a non-human mammal expressing human or humanized CD28 is provided. In some embodiments, the tissue-specific expression of human or humanized CD28 protein is provided.

In some embodiments, the expression of human or humanized CD28 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human CD28 protein can be detected by a variety of methods.

There are many analytical methods that can be used to detect exogenous DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized CD28 protein.

Vectors

The present disclosure relates to a targeting vector, comprising: a) a DNA fragment homologous to the 5' end of a region to be altered (5' arm), which is selected from the CD28 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the CD28 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000067.6; c) the DNA fragment homologous to the 3' end of the region to be altered (3' arm) is selected from the nucleotide sequences that have at least 90% homology to the NCBI accession number NC_000067.6.

In some embodiments, a) the DNA fragment homologous to the 5' end of a region to be altered (5' arm) is selected from the nucleotides from the position 60761678 to the position 60763007 of the NCBI accession number NC_000067.6; c) the DNA fragment homologous to the 3' end of the region to be altered (3' arm) is selected from the nucleotides from the position 60765309 to the position 60766648 of the NCBI accession number NC_000067.6.

In some embodiments, the length of the selected genomic nucleotide sequence in the targeting vector can be more than about 2 kb, about 2.5 kb, about 3 kb, about 3.5 kb, about 4 kb, about 4.5 kb, about 5 kb, about 5.5 kb, or about 6 kb.

In some embodiments, the region to be altered is exon 1, exon 2, exon 3, and/or exon 4 of CD28 gene (e.g., exon 2, and/or exon 3 of mouse CD28 gene).

The targeting vector can further include a selected gene marker.

In some embodiments, the sequence of the 5' arm is shown in SEQ ID NO: 34; and the sequence of the 3' arm is shown in SEQ ID NO: 36.

In some embodiments, the sequence is derived from human (e.g., 203726662-203729688 of NC_000002.12). For example, the target region in the targeting vector is a part or entirety of the nucleotide sequence of a human CD28, preferably exon 2 and/or exon 3 of the human CD28. In some embodiments, the nucleotide sequence of the humanized CD28 encodes the entire or the part of human CD28 protein with the NCBI accession number NP_006130.1 (SEQ ID NO: 29).

The disclosure also relates to a cell comprising the targeting vectors as described above.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous CD28 gene locus, a sequence encoding a region of an endogenous CD28 with a sequence encoding a corresponding region of human or chimeric CD28. In some embodiments, the replacement occurs in a germ cell, a somatic cell, a blastocyst, or a fibroblast, etc. The nucleus of a somatic cell or the fibroblast can be inserted into an enucleated oocyte.

FIG. 3 shows a humanization strategy for a mouse CD28 locus. In FIG. 3, the targeting strategy involves a vector comprising the 5' end homologous arm, human CD28 gene fragment, 3' homologous arm. The process can involve replacing endogenous CD28 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous CD28 sequence with human CD28 sequence.

Thus, in some embodiments, the methods for making a genetically modified, humanized animal, can include the step of replacing at an endogenous CD28 locus (or site), a nucleic acid encoding a sequence encoding a region of endogenous CD28 with a sequence encoding a corresponding region of human CD28. The sequence can include a region (e.g., a part or the entire region) of exon 1, exon 2, exon 3, and/or exon 4 of a human CD28 gene. In some embodiments, the sequence includes a region of exon 2, and exon 3 of a human CD28 gene (e.g., amino acids 28-150 of SEQ ID NO: 29). In some embodiments, the region is located within the extracellular region of CD28. In some embodiments, the endogenous CD28 locus is exon 2 and/or exon 3 of mouse CD28.

In some embodiments, the methods of modifying a CD28 locus of a mouse to express a chimeric human/mouse CD28 peptide can include the steps of replacing at the endogenous mouse CD28 locus a nucleotide sequence encoding a mouse CD28 with a nucleotide sequence encoding a human CD28, thereby generating a sequence encoding a chimeric human/mouse CD28.

In some embodiments, the nucleotide sequence encoding the chimeric human/mouse CD28 can include a first nucleotide sequence encoding an extracellular region of mouse CD28 (with or without the mouse or human signal peptide sequence); a second nucleotide sequence encoding an extracellular region of human CD28; a third nucleotide sequence encoding a transmembrane and a cytoplasmic region of a mouse CD28.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing a CD28 gene humanized animal model, involving the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudo pregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the methods described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized CD28 protein, e.g., in a physiologically appropriate manner, provide a variety of uses that include, but are not limited to, developing therapeutics for human diseases and disorders, and assessing the toxicity and/or assessing the efficacy of these human therapeutics in the animal models.

In various aspects, genetically modified animals are provided that express human or humanized CD28, which are useful for testing agents that can decrease or block the interaction between CD28 and CD28 ligands (e.g., CD80 or CD86) or assessing the interaction between CD28 and anti-human CD28 antibodies, testing whether an agent can increase or decrease the immune response, and/or determining whether an agent is an CD28 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-CD28 antibody for the treatment of cancer. The methods involve administering the anti-CD28 antibody (e.g., anti-human CD28 antibody) to the animal as described herein, wherein the animal has a tumor; and determining the inhibitory effects of the anti-CD28 antibody to the tumor. The inhibitory effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more cancer cells (e.g., human or mouse cancer cells) that are injected into the animal. In some embodiments, the anti-CD28 antibody, anti-CD80 antibody, or anti-CD86 antibody can prevent CD80 or CD86 from binding to CD28. In some embodiments, the anti-CD28 antibody, anti-CD80 antibody, or anti-CD86 antibody cannot prevent CD80 or CD86 from binding to CD28.

In some embodiments, the genetically modified animals can be used for determining whether an anti-CD28 antibody is a CD28 agonist or antagonist. In some embodiments, the methods as described herein are also designed to determine the effects of the agent (e.g., anti-CD28 antibodies) on CD28, e.g., whether the agent can stimulate immune cells or inhibit immune cells (e.g., T cells, CD4+ T cells, CD8+ T cells), whether the agent can increase or decrease the production of cytokines, whether the agent can activate or deactivate immune cells (e.g., T cells, plasma cells, or B cells), and/or whether the agent can upregulate the immune response or downregulate immune response. In some embodiments, the genetically modified animals can be used for determining the effective dosage of a therapeutic agent for treating a disease in the subject, e.g., cancer, or autoimmune diseases (e.g., multiple sclerosis, rheumatoid arthritis, and psoriasis). In some embodiments, the genetically modified animals can be used for determining whether an agent can inhibit transplantation rejection.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-CD28 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-CD28 antibody is designed for treating melanoma (e.g., advanced melanoma), non-small cell lung carcinoma (NSCLC), small cell lung cancer (SCLC), B-cell non-Hodgkin lymphoma, bladder cancer, and/or prostate cancer (e.g., metastatic hormone-refractory prostate cancer). In some embodiments, the anti-CD28 antibody is designed for treating hepatocellular, ovarian, colon, or cervical carcinomas. In some embodiments, the anti-CD28 antibody is designed for treating advanced breast cancer, advanced ovarian cancer, and/or advanced refractory solid tumor. In some embodiments, the anti-CD28 antibody is designed for treating metastatic solid tumors, NSCLC, melanoma, non-Hodgkin lymphoma, colorectal cancer, and multiple myeloma. In some embodiments, the anti-CD28 antibody is designed for treating melanoma, pancreatic carcinoma, mesothelioma, hematological malignancies (e.g., Non-Hodgkin's lymphoma, lymphoma, chronic lymphocytic leukemia), or solid tumors (e.g., advanced solid tumors). In some embodiments, the anti-CD28 antibody is designed for treating lung cancers.

In some embodiments, the anti-CD28 antibody is designed for treating various autoimmune diseases. Thus, the methods as described herein can be used to determine the effectiveness of an anti-CD28 antibody in inhibiting immune response.

The present disclosure also provides methods of determining toxicity of an antibody (e.g., anti-CD28 antibody). The methods involve administering the agent to the animal as described herein. The animal is then evaluated for its weight change, red blood cell count, hematocrit, and/or hemoglobin. In some embodiments, the agent can decrease the red blood cells (RBC), hematocrit, or hemoglobin by more than 20%, 30%, 40%, or 50%. In some embodiments, the animals can have a weight that is at least 5%, 10%, 20%, 30%, or 40% smaller than the weight of the control group (e.g., average weight of the animals that are not treated with the antibody).

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the CD28 gene function, human CD28 antibodies, drugs for human CD28 targeting sites, the drugs or efficacies for human CD28 targeting sites, the drugs for immune-related diseases and antitumor drugs.

Genetically Modified Animal Model with Two or More Human or Chimeric Genes

The present disclosure further relates to methods for generating genetically modified animal model with two or more human or chimeric genes. The animal can comprise a human or chimeric CD28 gene and a sequence encoding an additional human or chimeric protein.

In some embodiments, the additional human or chimeric protein can be programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD40, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), Signal regulatory protein α (SIRPα), or TNF Receptor Superfamily Member 4 (TNFRSF4 or OX40).

The methods of generating genetically modified animal model with two or more human or chimeric genes (e.g., humanized genes) can include the following steps:

(a) using the methods of introducing human CD28 gene or chimeric CD28 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, BTLA, PD-L1, CD27, CD40, CD47, CD137, CD154, TIGIT, TIM-3, GITR, SIRPa, or OX40. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024, PCT/CN2017/110494, PCT/CN2017/110435, PCT/CN2017/120388, PCT/CN2018/081628, PCT/CN2018/081629; each of which is incorporated herein by reference in its entirety.

In some embodiments, the CD28 humanization is directly performed on a genetically modified animal having a human or chimeric PD-1, CTLA-4, BTLA, PD-L1, CD27, CD40, CD47, CD137, CD154, TIGIT, TIM-3, GITR, SIRPα, or OX40 gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-CD28 antibody and an additional therapeutic agent for the treatment of cancer. The methods include administering the anti-CD28 antibody and the additional therapeutic agent to the animal, wherein the animal has a tumor; and determining the inhibitory effects of the combined treatment to the tumor. In some embodiments, the additional therapeutic agent is an antibody that specifically binds to PD-1, CTLA-4, BTLA, PD-L1, CD27, CD40, CD47, CD137, CD154, TIGIT, TIM-3, GITR, SIRPα, or OX40. In some embodiments, the additional therapeutic agent is an anti-CTLA4 antibody (e.g., ipilimumab), an anti-PD-1 antibody (e.g., nivolumab), or an anti-PD-L1 antibody.

In some embodiments, the animal further comprises a sequence encoding a human or humanized PD-1, a sequence encoding a human or humanized PD-L1, or a sequence encoding a human or humanized CTLA-4. In some embodiments, the additional therapeutic agent is an anti-PD-1 antibody (e.g., nivolumab, pembrolizumab), an anti-PD-L1 antibody, or an anti-CTLA-4 antibody. In some embodiments, the tumor comprises one or more tumor cells that express CD80, CD86, PD-L1, and/or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), advanced breast cancer, advanced ovarian cancer, and/or advanced refractory solid tumor. In some embodiments, the combination treatment is designed for treating metastatic solid tumors, NSCLC, melanoma, B-cell non-Hodgkin lymphoma, colorectal cancer, and multiple myeloma. In some embodiments, the combination treatment is designed for treating melanoma, carcinomas (e.g., pancreatic carcinoma), mesothelioma, hematological malignancies (e.g., Non-Hodgkin's lymphoma, lymphoma, chronic lymphocytic leukemia), or solid tumors (e.g., advanced solid tumors). In some embodiments, the combination treatment is designed for treating lung cancers.

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor, from the patient.

EXAMPLES

The invention is further described in the following examples, which do not limit the scope of the invention described in the claims.

Materials and Methods

The following materials were used in the following examples.

C57BL/6 mice were purchased from the China Food and Drugs Research Institute National Rodent Experimental Animal Center.

EcoRI, BamHI, BbsI, HindIII, XhoI restriction enzymes were purchased from NEB (Catalog numbers: R3101M, R3136M, R0539L, R3104M, R0146S).

Ambion in vitro transcription kit was purchased from Ambion (Catalog number: AM1354).

UCA kit was obtained from Beijing Biocytogen Co., Ltd. (Catalog number: BCG-DX-001).

TOP10 competent cells were purchased from the Tiangen Biotech (Beijing) Co. (Catalog number: CB104-02).

Cas9 mRNA was purchased from SIGMA (Catalog number: CAS9MRNA-1EA).

AIO kit was obtained from Beijing Biocytogen Co., Ltd. (Catalog number: BCG-DX-004).

The pHSG299 was purchased from Takara (Catalog number: 3299).

Purified NA/LE Hamster Anti-Mouse CD3e (mCD3) antibody was purchased from BD (Catalog number: 553057).

PerCP/Cy5.5 anti-mouse TCR β chain (mTcR β PerCP) was purchased from Biolegend (Catalog number: 109228).

PE anti-mouse CD28 antibody (mCD28 PE) was purchased from Biolegend (Catalog number: 102105).

APC anti-human CD28 antibody (hCD28 APC) was purchased from Biolegend (Catalog number: 302912).

Example 1

Design of sgRNA for CD28 Gene

The 5'-terminal targeting sites (sgRNA1 to sgRNA12) and the 3'-terminal targeting sites (sgRNA13 to sgRNA20) were designed and synthesized.

The 5'-terminal targeting sites were located in exon 2 of mouse CD28 gene. The 3'-terminal targeting sites were located in exon 3 of mouse CD28 gene. The targeting site sequences on CD28 for each sgRNA are shown below:

```
sgRNA-1 target sequence (SEQ ID NO: 1):
5'-ctcggcattcgagcgaaactggg-3' sgRNA-2 target sequence (SEQ ID NO: 2):
5'-tgccgagttcaactgcgacgggg-3' sgRNA-3 target sequence (SEQ ID NO: 3):
5'-cgctgttcacgcccttgtacagg-3' sgRNA-4 target sequence (SEQ ID NO: 4):
5'-caagggcgtgaacagcgacgtgg-3' sgRNA-5 target sequence (SEQ ID NO: 5):
5'-atccccgtcgcagttgaactcgg-3' sgRNA-6 target sequence (SEQ ID NO: 6):
5'-aaacagtgacgttccgtctctgg-3' sgRNA-7 target sequence (SEQ ID NO: 7):
5'-cccggaattcctttgcgagaagg-3' sgRNA-8 target sequence (SEQ ID NO: 8):
5'-gcttgtggtagatagcaacgagg-3' sgRNA-9 target sequence (SEQ ID NO: 9):
5'-cgagcgaaactggggctgatagg-3' sgRNA-10 target sequence (SEQ ID NO: 10):
5'-tggaagtctgtgtcgggaatggg-3' sgRNA-11 target sequence (SEQ ID NO: 11):
5'-cgttgctatctaccacaagcagg-3' sgRNA-12 target sequence (SEQ ID NO: 12):
5'-agcgacgtggaagtctgtgtcgg-3' sgRNA-13 target sequence (SEQ ID NO: 13):
5'-gactcgatcatctaagctggtgg-3' sgRNA-14 target sequence (SEQ ID NO: 14):
5'-caaattcgcctctgatgtacagg-3' sgRNA-15 target sequence (SEQ ID NO: 15):
5'-caagactcgatcatctaagctgg-3' sgRNA-16 target sequence (SEQ ID NO: 16):
5'-gatgatcgagtcttgctctttgg-3' sgRNA-17 target sequence (SEQ ID NO: 17):
5'-agtcatctcctaagctgtfttgg-3' sgRNA-18 target sequence (SEQ ID NO: 18):
5'-aaacacaacatgtgggttaaagg-3' sgRNA-19 target sequence (SEQ ID NO: 19):
5'-atttctgtcctgtacatcagagg-3' sgRNA-20 target sequence (SEQ ID NO: 20):
5'-ctctgaaaaacacaacatgtggg-3'
```

Example 2

Testing sgRNA Activity

The UCA kit was used to detect the activities of sgRNAs (FIGS. 1A-1B and Table 4). The results show that the guide sgRNAs had different activities. Two of them sgRNA4 (SEQ ID NO: 4) and sgRNA17 (SEQ ID NO: 17) were selected for further experiments.

The synthesized sgRNA sequences based on sgRNA4 and sgRNA17 target sequences are listed in the following table:

TABLE 3

| sgRNA4 and sgRNA17 sequences | | |
|---|---|---|
| sgRNA4 sequences | | |
| SEQ ID NO: 21 | Upstream: | 5'-GCGTGAACAGCGACG-3' |
| SEQ ID NO: 22 | Downstream: | 5'-CGTCGCTGTTCACGC-3' |
| sgRNA17 sequences | | |
| SEQ ID NO: 23 | Upstream: | 5'-TCATCTCCTAAGCTGTTT-3' |
| SEQ ID NO: 24 | Downstream: | 5'-AAACAGCTTAGGAGATGA-3' |

TABLE 4

Activities of sgRNAs

| 5'-terminal targeting sites | | 3'-terminal targeting sites | |
|---|---|---|---|
| sgRNAs | Normalized Activities | sgRNAs | Normalized Activities |
| Negative control (con) | 1.00 | Negative control (con) | 1.00 |
| Positive control (pc) | 128.96 | Positive control (pc) | 513.82 |
| sgRNA-1 | 89.30 | sgRNA-13 | 102.01 |
| sgRNA-2 | 163.83 | sgRNA-14 | 3.36 |
| sgRNA-3 | 41.13 | sgRNA-15 | 32.93 |
| sgRNA-4 | 76.19 | sgRNA-16 | 28.50 |
| sgRNA-5 | 28.99 | sgRNA-17 | 101.40 |
| sgRNA-6 | 11.83 | sgRNA-18 | 4.73 |
| sgRNA-7 | 9.51 | sgRNA-19 | 20.52 |
| sgRNA-8 | 36.68 | sgRNA-20 | 27.05 |
| sgRNA-9 | 73.43 | | |

TABLE 4-continued

Activities of sgRNAs

| 5'-terminal targeting sites | | 3'-terminal targeting sites | |
|---|---|---|---|
| sgRNAs | Normalized Activities | sgRNAs | Normalized Activities |
| sgRNA-10 | 90.36 | | |
| sgRNA-11 | 23.16 | | |
| sgRNA-12 | 78.26 | | |

Example 3

Constructing pT7-sgRNA G2 Plasmids

A map of pT7-sgRNA G2 vector is shown in FIG. 2. The DNA fragment containing T7 promoter and sgRNA scaffold was synthesized, and linked to the backbone vector by restriction enzyme digestion (EcoRI and BamHI) and ligation. The target plasmid sequence was confirmed by the sequencing results.

The DNA fragment containing the T7 promoter and sgRNA scaffold (SEQ ID NO: 25) is shown below:

GAATTCTAATACGACTCACTATAGGGGGTCTTCGAGAAGACCTGTTTTAG

AGCTAGAAATAGCAAGTTAAAATAAGGCTAGTCCGTTATCAACTTGAAAA

AGTGGCACCGAGTCGGTGCTTTTAAAGGATCC

Example 4

Constructing Recombinant Expression Vectors pT7-CD28-4 and pT7-CD28-17

TAGG was added to the 5' end of SEQ ID NO: 21 and SEQ ID NO: 23 to obtain a forward oligonucleotide sequence, and AAAC was added to the 5' end of the complementary strand (SEQ ID NO: 22 and SEQ ID NO: 24) to obtain a reverse oligonucleotide sequence.

```
sgRNA-4 forward oligonucleotide:
                            (SEQ ID NO: 51)
5'-TAGGGCGTGAACAGCGACG-3' sgRNA-4 reverse oligonucleotide:
                            (SEQ ID NO: 52)
5'-AAACCGTCGCTGTTCACGC-3' sgRNA-17 forward oligonucleotide:
                            (SEQ ID NO: 53)
5'-TAGGTCATCTCCTAAGCTGTTT-3' sgRNA17 reverse oligonucleotide:
                            (SEQ ID NO: 54)
5'-AAACAAACAGCTTAGGAGATGA-3'
```

After annealing, they were respectively ligated to pT7-sgRNA G2 plasmid (linearized with BbsI) to obtain the expression vectors pT7-CD28-4 and pT7-CD28-17. The ligation reaction was set up as follows:

TABLE 5

| The ligation reaction mix (10 µL) | |
|---|---|
| sgRNA after annealing | 1 µL (0.5 µM) |
| pT7-sgRNA G2 vector | 1 µL (10 ng) |

TABLE 5-continued

| The ligation reaction mix (10 µL) | |
|---|---|
| T4 DNA Ligase | 1 µL (5 U) |
| 10 × T4 DNA Ligase buffer | 1 µL |
| 50% PEG4000 | 1 µL |
| H$_2$O | Add to 10 µL |

The ligation reaction was carried out at room temperature for 10 to 30 minutes. The ligation product was then transferred to 30 µL of TOP10 competent cells. The cells were then plated on a petri dish with Kanamycin, and then cultured at 37° C. for at least 12 hours and then two clones were selected and added to LB medium with Kanamycin (5 ml), and then cultured at 37° C. at 250 rpm for at least 12 hours.

Clones were randomly selected and sequenced to verify their sequences. The vectors with correct sequences were selected for subsequent experiments.

Example 5

Sequence Design for Humanized CD28

A partial coding sequence of the mouse CD28 gene (Gene ID: 12487) from exons 2-3 (based on the transcript of NCBI accession number NM_007642.4→NP_031668.3 whose mRNA sequence is shown in SEQ ID NO: 26, and the corresponding protein sequence is shown in SEQ ID NO: 27) was replaced with a corresponding coding sequence of human homologous CD28 gene (Gene ID: 940) (based on the transcript of NCBI accession number NM_006139.3→NP_006130.1, whose mRNA sequence was shown in SEQ ID NO: 28, and the corresponding protein sequence is shown in SEQ ID NO: 29). The comparison between the mouse CD28 and human CD28 is shown in FIG. 11, and the finally obtained humanized CD28 gene is shown in FIG. 4. The humanized mouse CD28 gene DNA sequence (chimeric CD28 gene DNA) is shown in SEQ ID NO: 30.

aaacttgagaactttcagtgtagtcatcattccaagaagagctattaata tatcttttctgccaagggactaactttgttggaggtctgttcagttggc taattaattcactttgatttcagggcaatggaattattattcttatgctc ctaactaaatgttttttcccttcagaaaacaagattttggtaaagcagt cgccc<u>atgcttgtagcgtacgacaatgcggtcaaccttagctgcaagtat</u>

<u>tcctacaatctcttctcaagggagttccgggcatcccttcacaaaggact</u>

<u>ggatagtgctgtggaagtctgtgttgtatatgggaattactcccagcagc</u>

<u>ttcaggtttactcaaaaacggggttcaactgtgatgggaaatttgggcaat</u>

<u>gaatcagtgacattctacctccagaatttgtatgttaaccaaacagatat</u>

-continued ttacttctgcaaaattgaagttatgtatcctcctccttacctagacaatg agaagagcaatggaaccattatccatgtgaaaggtaacatacaactttac cagtgtaccaccctaaagtaatggttttcaaatgcagtcctgaaaactgg gttgtggtcagtggtggggttgaataaggcctaagtgatttgatactaac aaagacaaataatgttttcagaaaaattttccctttactgtagaggaga ttcaaggttatattttgaatatcttttattttcctttgctgacattgagcg ggagagtaagtgatgaagttaccgcatgtgggaacagatcattttctcc attccagtggatcatggcagaaaagaggttaccattaaaatgtaagccca ggtgccctcaagtaacagctgggtctaatggttaagactcaggaagact cacttctatttctaattaattcttttttgtgctccataatcttcctctg taaaagtacctttccatttcttttccttccttccttccttccttcctt ccttccttccttttcttttcttttcttttcttttttttgagacggac tctcgctctgtcgcccaggctggagtgcagtggcgggatctcagttcact gcaagctctgcctcccgggttcacgtcattctcctgcctcagcctcccga tcagctgggactacaggcccgccaccacgcctggcttatttttgtata tttatttattttatttttaattaattaattttttttttgagaggggag tcttgctctgtcgcccaggctggaatgcggtggcgcgatctcggctcact gcaagctccgcctcccaggttcatgccattctcctgcctcagcctcctga gtagctgggactacaggtacctgccaccatgcccggctaattttttgtat ttttagtagacagggtttcaccttgttagccaggatggtctcgatttcct gacctcgtgacccgcccgtgttggcctcccaaagtgctgggattacaggc gtgagccaccgcgcccagccatttttttgtacttttagtagagacggggtt tcaccgtgttagcaaggatggtctcaatctcctgacctcgtgatctgccc acctgggcctcccaaagtgctgtgattacaggcgtaagccaccgcgccca gccccgtacctttccatttctaaaatatacaaagaatgctggactagaaa ccgggggacataaaatttgctattaatcaactgtgtgatcttggataagt cacctaacttttttcatagtcaaaaactcagtacaactgttaagcagtatt tgtgaattagtgaaaataagtctactgaacttttgttgatgttatgttct gcctaaatgttagggagaaaaatcatgattccccaactcagaagaataca gtattggtagcaacaagtaaagtttgatttttggtatactttgtggata tatcatagcttttcatttttgtggaatgataataagaaacacatatgttc agttttgtactgaatcctagcataatgccaatgaatggttttcttcaat gctggaacagagccatgctgatgaaaaataggatactaaataaggaaaga attgttaatgtggcagataagcttttgttgttctggcaaaatagagacaat taatgtgtgaatattttgtttgctgagtcctatttagatttctaatatct gtaatatccaaacagaatattttaattgtatcaagtcaaaggttaaaaaa ttatgctattttgcttgtagctaagagtgaaatattttttcctatatgaa aggcatgctactttaggatagtattttatatatatgtatacacacatata cacatatcatttatgttagaactgagaaggacaccaatgatcctgtactt agtaattttcaatcctatctgtatattataaatctgagtaggttttaaaa gaaataccaatgcctagttccagccctgagattctgatgtaattgatatg ggttgaggaagggtgctggacatcagtatattttcaaactttctcggat aatttattgtgcagctaggatggaaaatcaatggactagaggattttttgg tatgctttctagttctaattttctctaattttgaatagaattctataggt tccttctcatcccctttttgattcctaaagatacaaagtgatttgtttgtc attatataatctatgagacagggttggaactagaaatttatcctctgatt agcagtccagtgttctgactgccatattaggctgatgattttcttaaggc ttgaaaacatgcatattatttaacttattccaaggatgcagtttagggtc tagattaactatcttctgatgggagaaacggataaagttaggttaaggcc attggaagtcaccgttttgaatcacacagtagaatccacaaagtcaagtg aatacaagtctaccagtgtaccatcctaacgtaatggctttcaactgtgg tcgtgaaaactgaccagatcatggtcagtggtggggttgggtaagtctca aagaggaaatctattcactctaagctggtgatatgtttaatattttatt tctttcacatttttctctgatgttcacaaggaaggaaatgcactcaattg ctattcctgtatcatttaatccactctattttgttttcagggaaacacc tttgtccaagtcccctatttcccggaccttctaagctgtttgggcactgg tcgtggttgctggagtcctgttttgttatggcttgctagtgacagtggct ctttgtgttatctgggtaagaggagcaacattgcttttatgtaacttctc tgcgcctgccctctgactatattaagactctggcctgtatcttttctacg ttaaagcaaatgacgcttttcagtctgtcca SEQ ID NO: 30 shows only the modified portion of DNA sequence, wherein the italicized underlined region is from human CD28.

The coding region sequence, mRNA sequence and the encoded protein sequence thereof of the modified humanized CD28 are respectively shown in SEQ ID NO: 31, SEQ ID NO: 32, and SEQ ID NO: 33.

To the extent that either human CD28 or mouse CD28 has more than one isoforms or transcripts, the methods as described herein can be applied to other isoforms or transcripts.

Example 6 pClon-2G-CD28 Plasmids

Based on the sequences, a targeting strategy for generating the humanized CD28 mouse model is shown in FIG. 3. The 5' homologous arm comprises nucleic acid 60761678-60763007 of NCBI Accession No. NC_000067.6 (SEQ ID NO: 34). The 3' homologous arm comprises nucleic acid 60765309-60766648 of NCBI Accession No. NC_000067.6 (SEQ ID NO: 36). The human sequence corresponds to 203726662-203729688 of NCBI Accession No. NC_000002.12 (SEQ ID NO: 35).

Primers for amplifying the 4 recombination fragments (LR, A1, A2, RR) and related sequences were designed. Among them, the LR fragment corresponds to the 5' homologous arm, the RR fragment corresponds to the 3' homologous arm, and the A1+A2 fragments correspond to the human CD28 sequence.

The primers are shown in the table below.

TABLE 6

Primers for recombination fragments

| Fragment | Length (bp) | Primer sequence |
|---|---|---|
| LR | 1360 bp | F: 5'-atcgctcgagcggtcagctatttaggtggtgtagc-3' (SEQ ID NO: 50)<br>R: 5'-ttgtcgtacgctacaagcatgggcgactgctttaccaaaatcttg-3' (SEQ ID NO: 37) |
| A1 | 1200 bp | F: 5'-ttttggtaaagcagtcgcccatgcttgtagcgtacgacaatgcgg-3' (SEQ ID NO: 38)<br>R: 5'-cgggcatggtggcaggtacctgtagtcccagctactcaggaggct-3' (SEQ ID NO: 39) |
| A2 | 1907 bp | F: 5'-cctgagtagctgggactacaggtacctgccaccatgcccggctaa-3' (SEQ ID NO: 40)<br>R: 5'-accagtgcccaaaacagcttagaaggtccgggaaatagggg actt-3' (SEQ ID NO: 41) |
| RR | 1370 bp | F: ccctatttcccggaccttctaagctgttttgggcactggtcgtgg-3' (SEQ ID NO: 42)<br>R: 5'-atcgccatggtgggtgaagagtagcaagataaggggt-3' (SEQ ID NO: 43) |

The LR and RR fragments were prepared by using C57BL/6 mouse genomic DNA as a template. A1 and A2 fragments were obtained by using human genomic DNA as a template. Fragments LR and A1 were linked by PCR, and A2 and RR were also linked by PCR (reaction conditions are shown in Tables 7 and 8). After the sequences were verified by sequencing, the LR+A1 fragment (XhoI+KpnI) and the A2+RR fragment (KpnI+NcoI) were ligated to the pClon-2G plasmid from the AIO kit to obtain the pClon-2G-CD28 vector.

TABLE 7

The PCR reaction (20 μL)

| | |
|---|---|
| 2× PCR buffer | 10 μL |
| dNTP (2 mM) | 4 μL |
| Upstream primer (10 μM) | 0.6 μL |
| Downstream primer (10 μM) | 0.6 μL |
| Mouse tail genomic DNA | 100 ng |
| KOD-FX (1 U/μL) | 0.4 μL |
| H₂O | Add to 20 μL |

TABLE 8

The PCR reaction conditions

| Temperature | Time | Cycles |
|---|---|---|
| 94° C. | 5 min | 1 |
| 98° C. | 30 sec | 35 |
| 62° C. | 30 sec | |
| 68° C. | 30 sec | |
| 68° C. | 10 min | 1 |
| 4° C. | 10 min | 1 |

When fragments LR and A1 were ligated, Primer F in Table 7 was SEQ ID NO: 50, Primer R was SEQ ID NO: 39, and the DNA template was the recovered PCR amplification product of the LR fragment and A1 fragment. When fragments A2 and RR were ligated, Primer F was SEQ ID NO: 40, primer R was SEQ ID NO: 43, and the DNA template was the recovered PCR amplification product of the A2 fragment and RR fragment.

Example 7

Verification of pClon-2G-CD28 Vectors

Figure 5:
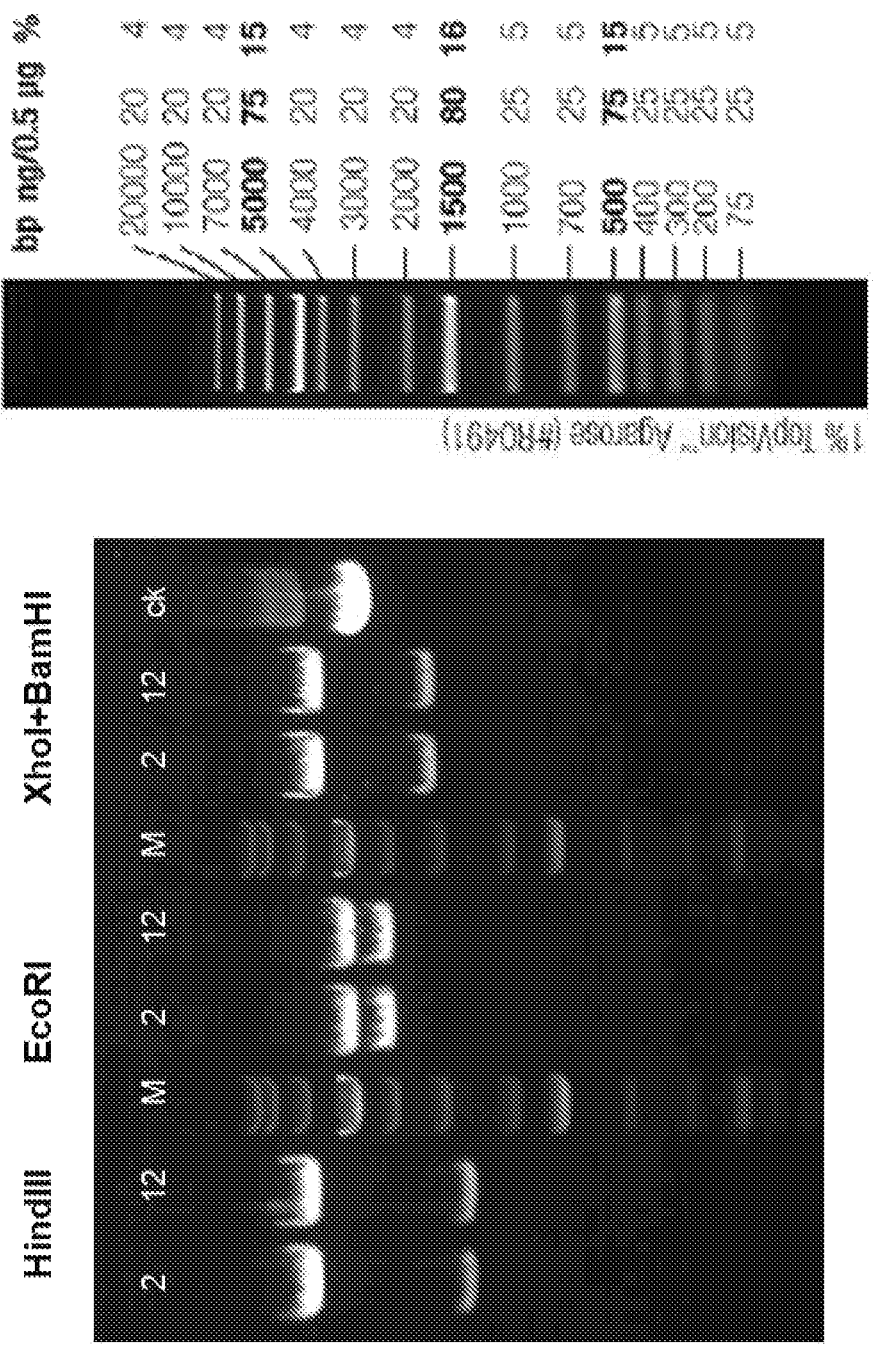
FIG. 5 shows the restriction enzymes digestion results of the targeting plasmid pClon-2G-CD28 by three sets of restriction enzymes.

Two pClon-2G-CD28 clones were randomly selected and tested by three sets of restriction enzymes. Among them, HindIII should generate 5947 bp+2460 bp fragments; EcoRI should generate 4633 bp+3774 bp fragments; XhoI+BamHI should generate 5525 bp+2882 bp fragments. Plasmids 2 and 12 had the expected results (FIG. 5). The sequences of Plasmid 2 were further confirmed by sequencing.

Example 8

Microinjection and Embryo Transfer

The pre-mixed Cas9 mRNA, pClon-2G-CD28 plasmid and in vitro transcription products of pT7-CD28-4 , pT7-CD28-17 plasmids were injected into the cytoplasm or nucleus of mouse fertilized eggs (C57BL/6 background) with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The mouse population was further expanded by cross-mating and self-mating to establish stable mouse lines. These humanized mice were named as B-hCD28.

Example 9

Verification of Genetic Modification

1. Genotype Determination for F0 Generation Mice

PCR analysis was performed using mouse tail genomic DNA of F0 generation mice. Primer L-GT-F is located on the left side of 5' homologous arm, Primer R-GT-R is located on the right side of 3' homologous arm, and both R-GT-F and L-GT-R are located within the second intron.

```
5' end primers:
Upstream: L-GT-F (SEQ ID NO: 44):
5'-ggtagctcttagcatgcttccccag-3'

Downstream: L-GT-R (SEQ ID NO: 45):
5'-gccagaacacaaaagcttatctgcca-3'

3' end primers:
Upstream: R-GT-F (SEQ ID NO: 46):
5'-gaatgctggactagaaaccggggg-3'

Downstream: R-GT-R (SEQ ID NO: 47):
5'-cttagagctagagctgccctgtccc-3'
```

Figure 6A:
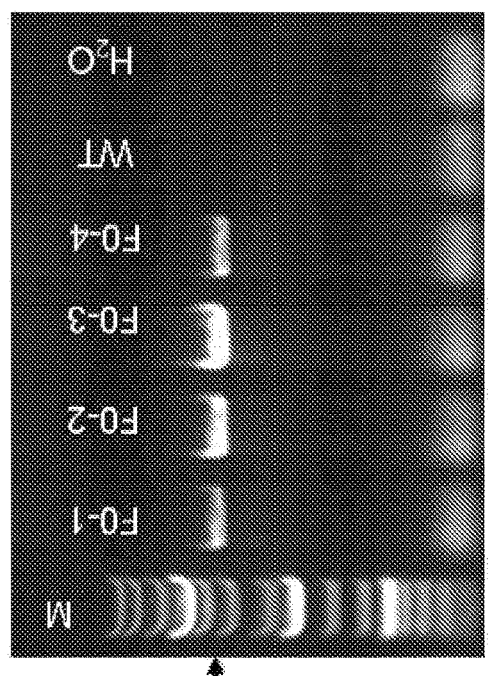
FIGS. 6A-6B show PCR identification results of samples collected from tails of F0 generation mice. WT is wildtype. Mice labeled with F0-1, F0-2, F0-3, and F0-4 are F0 generation humanized CD28 mice.
Figure 6B:
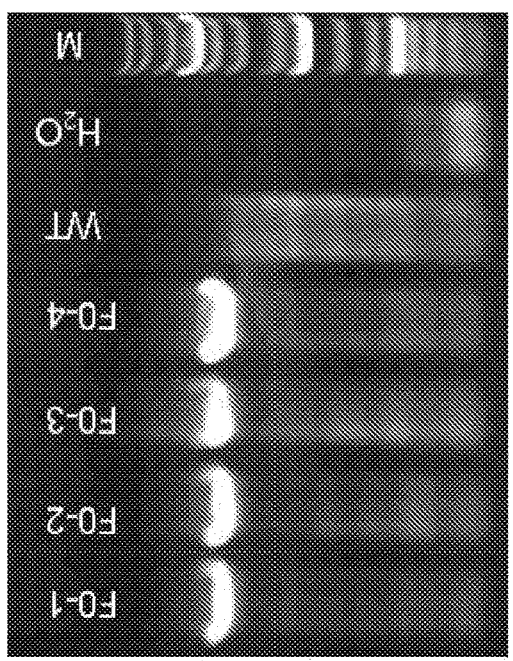

If the desired human sequence was inserted into the correct positions in the genome, PCR experiments using the above primers should generate only one band. The first pair of primers should produce a band of about 3439 bp, the second pair of primers should produce a band of about 3128 bp. The results for F0 generation mice are shown in FIGS. 6A-6B. Among these tested mice, F0-1, F0-2, F0-3, F0-4 were positive.

TABLE 9

The PCR reaction (20 μL)

| | |
|---|---|
| 2× PCR buffer | 10 μL |
| dNTP (2 mM) | 4 μL |
| Upstream primer (10 μM) | 0.6 μL |
| Downstream primer (10 μM) | 0.6 μL |
| Mouse tail genomic DNA | 100 ng |
| KOD-FX (1 U/μL) | 0.4 μL |
| H$_2$O | Add to 20 μL |

TABLE 10

The PCR reaction conditions

| Temperature | Time | Cycles |
|---|---|---|
| 94° C. | 2 min | 1 |
| 98° C. | 10 sec | 15 |
| 67° C. (−0.7° C./cycle) | 30 sec | |
| 68° C. | 1 kb/min | |
| 98° C. | 10 sec | 25 |
| 56° C. | 30 sec | |
| 68° C. | 1 kb/min | |
| 68° C. | 10 min | 1 |
| 4° C. | 10 min | 1 |

2. Genotype Determination for F1 Generation Mice

Figure 7B:
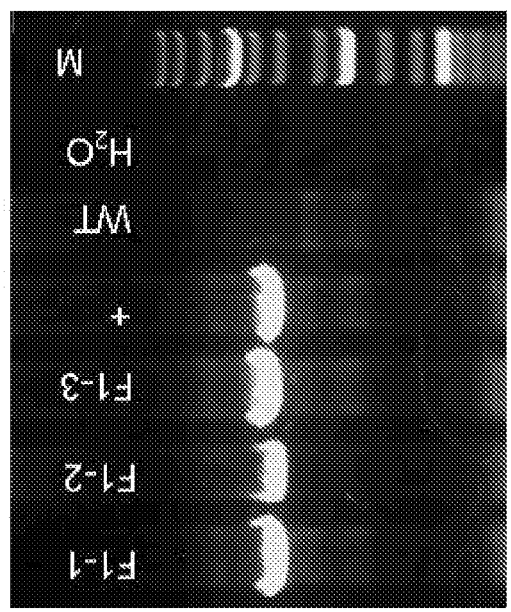
FIGS. 7A-7B show PCR identification results of samples collected from tails of F1 generation mice. WT is wildtype; + is positive control. Mice labeled with F1-1, F1-2, and F1-3 are F1 generation humanized CD28 mice.
Figure 7A:
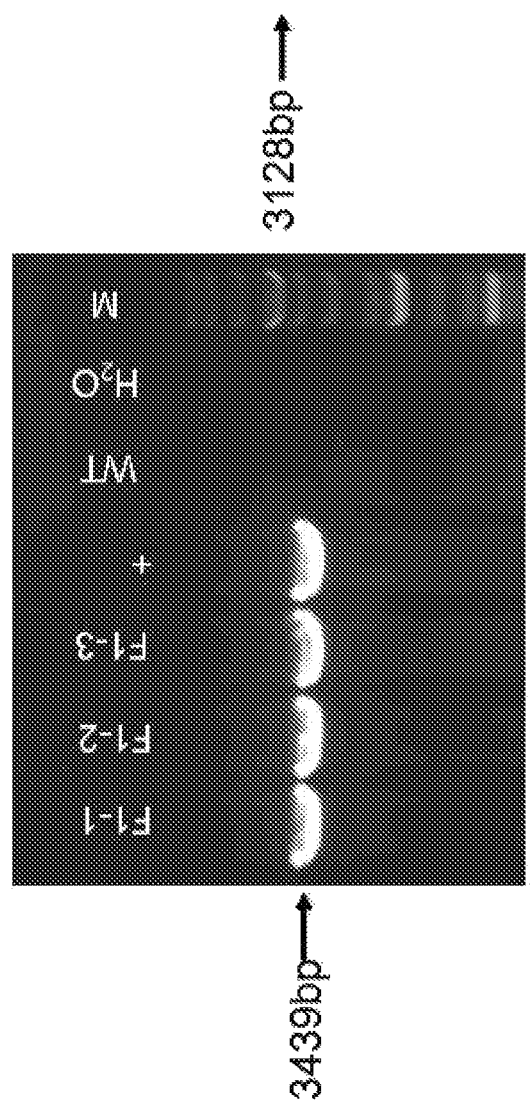

Positive F0 generation mice were mated with wild-type mice to obtain F1 generation mice. PCR was performed on the genomic DNA of three F1 generation mice. The results are shown in FIGS. 7A-7B. Mice labeled with F1-1, F1-2, and F1-3 were positive mice.

The results indicate that the humanized gene in the CD28 humanized mice can be stably passed to the next generation.

3. Expression Level Analysis in Humanized Mice

One humanized heterozygous mouse was selected. One wildtype mouse in the same background was used as the control.

7.5 μg of anti-mCD3 antibody was injected intraperitoneally to the mice. The spleens were collected 24 hours after the injection, and the spleen samples were grinded. The samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed with PBS and tested in FACS.

The cells were then stained with (1) PE anti-mouse CD28 (mCD28 PE) and PerCP/Cy5.5 anti-mouse TCR β chain (mTcRβ PerCP), or (2) human antibody APC anti-human CD28 (hCD28 APC) and PerCP/Cy5.5 anti-mouse TCR β chain (mTcRβ PerCP) antibody. The cells were washed with PBS again and the protein expression was measured by flow cytometry.

Figures 8A, 8B, 8C, 8D:
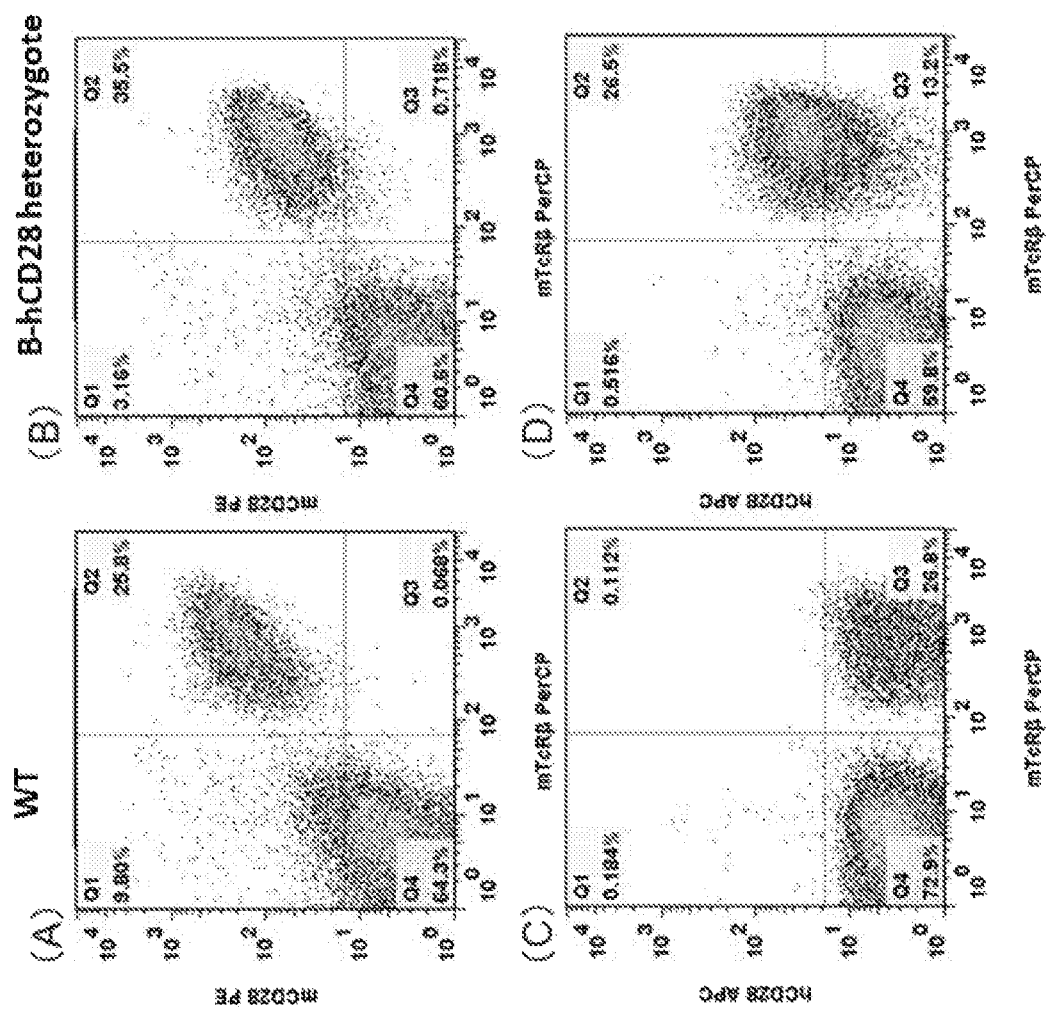
FIGS. 8A-8D are flow cytometry results of a wildtype mouse and a heterozygous humanized CD28 mouse. Anti-mCD3 antibody was used to activate spleen cells. Flow cytometry was performed with 1) antibody against mouse CD28 (mCD28 PE) (FIGS. 8A and 8B); or 2) antibody against human CD28 (hCD28 APC) (FIGS. 8C and 8D). In the control group, spleen cells that express human or humanized CD28 were not detected. Humanized CD28 was detected on spleen cells in the heterozygous humanized CD28 mouse.

The results are shown in FIGS. 8A-8D. In the control groups, no spleen cells stained with hCD28 APC were detected (FIG. 8C); in contrast, spleen cells stained with hCD28 APC were observed in heterozygous humanized CD28 mice (FIG. 8D).

Example 10

CD28 Knockout Mice

Since the cleavage of Cas9 results in DNA double strands break, and the homologous recombination repair may result in insertion/deletion mutations, it is possible to obtain CD28 knockout mice by the methods described herein. A pair of primers was thus designed to target the left side of the 5' target site and the right side of the 3' target site:

```
                                   (SEQ ID NO: 48)
5'-CACGCTCCTGTCTTCCCATTCAGAG-3'

(SEQ ID NO: 49)
5'-TTGGTGCCTTCTGGGAAACAGAACTC-3'
```

For wildtype mice, there should be no PCR band. There should be only one band (about 500 bp) for CD28 knockout mice.

Figure 9:
FIG. 9 shows PCR results for CD28 knockout mice. + is positive control. M is the marker. WT is the wildtype. F0-KO-1, F0-KO-2, F0-KO-3, F0-KO-4, and F0-KO-5 were CD28 knockout mice.

FIG. 9 shows the PCR results. F0-KO-1, F0-KO-2, F0-KO-3, F0-KO-4, and F0-KO-5 were F0 generation heterozygous CD28 knockout mice.

Example 11

Mice with Two or More Humanized Genes

Mice with the humanized CD28 gene (e.g., animal model with humanized CD28 prepared using the methods as described in the present disclosure) can also be used to prepare an animal model with double-humanized or multi-humanized genes. For example, in Example 8, the embryonic stem cell used in the microinjection and embryo transfer process can be selected from the embryos of other genetically modified mice (e.g., humanized PD-1 mice), so as to obtain double- or multiple-gene modified mouse models. The fertilized eggs of B-hCD28 mice can also be further genetically engineered to produce mouse lines with one or more humanized or otherwise genetically modified mouse models. In addition, the humanized CD28 animal model homozygote or heterozygote can be mated with other genetically modified homozygous or heterozygous animal models (or through IVF), and the progeny can be screened. According to the Mendelian law, there is a chance to obtain the double-gene or multiple-gene modified heterozygous animals, and then the heterozygous animals can be mated with each other to finally obtain the double-gene or multiple-gene modified homozygotes.

Example 12

Methods Based on Embryonic Stem Cell Technologies

The non-human mammals described herein can also be prepared through other gene editing systems and approaches, including but not limited to: gene homologous recombination techniques based on embryonic stem cells (ES), zinc finger nuclease (ZFN) techniques, transcriptional activator-like effector factor nuclease (TALEN) technique, homing endonuclease (megakable base ribozyme), or other techniques.

Figure 10:
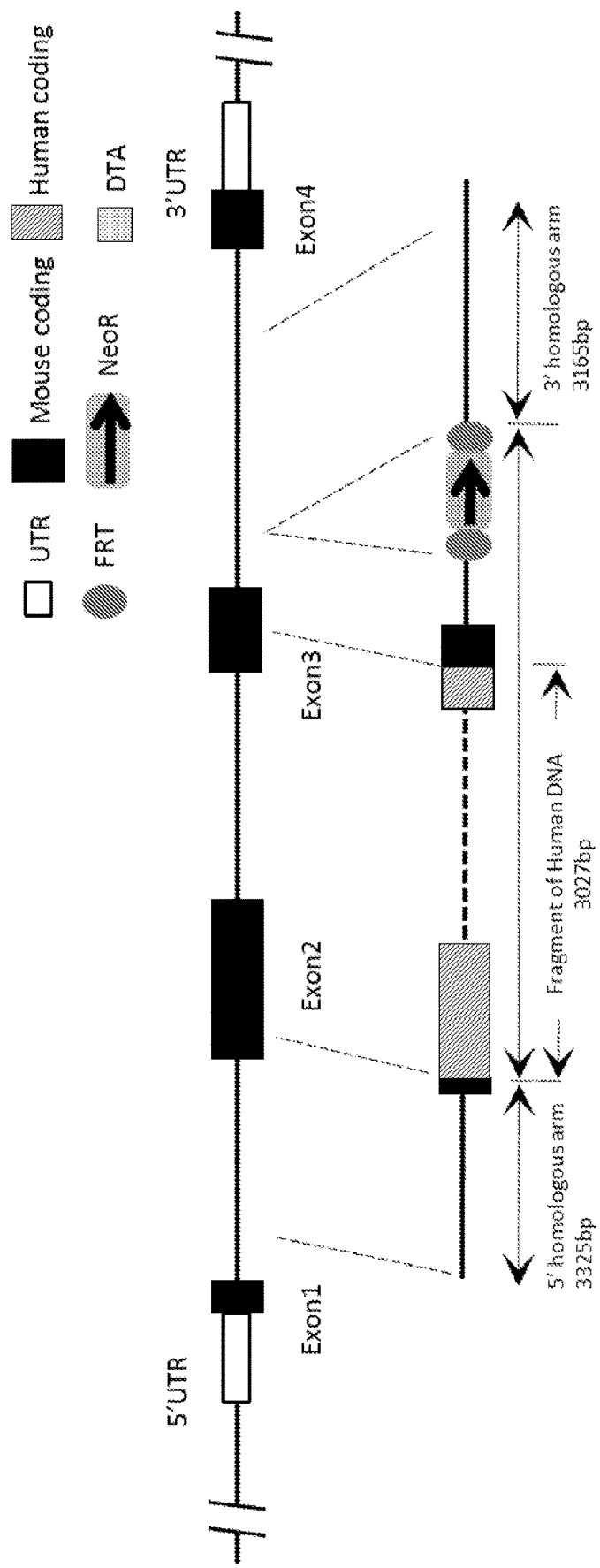
FIG. 10 is a schematic diagram showing gene targeting strategy based on embryonic stem cells.

Based on the CD28 transcript and the corresponding protein sequence and the humanized CD28 mouse gene map as shown in FIG. 4, a targeting strategy for generating the humanized CD28 mouse model with Embryonic Stem Cell Technologies is developed (FIG. 10). Since the objective is to replace exons 2-3 of the mouse CD28 gene in whole or in part with the corresponding sequence in human CD28 gene, a recombinant vector that contains a 5' homologous arm (3325 bp), a 3' homologous arm (3165 bp) and a sequence fragment from human CD28 (3027 bp) is designed. The vector can also contain a resistance gene for positive clone screening, such as neomycin phosphotransferase coding sequence Neo. On both sides of the resistance gene, two site-specific recombination systems in the same orientation, such as Frt or LoxP, can be added. Furthermore, a coding gene with a negative screening marker, such as the diphtheria toxin A subunit coding gene (DTA), can be constructed downstream of the recombinant vector 3' homologous arm.

Vector construction can be carried out using methods known in the art, such as enzyme digestion and so on. The recombinant vector with correct sequence can be next transfected into mouse embryonic stem cells, such as C57BL/6 mouse embryonic stem cells, and then the recombinant vector can be screened by positive clone screening gene. The cells transfected with the recombinant vector are next screened by using the positive clone marker gene, and Southern Blot technique can be used for DNA recombination identification. For the selected correct positive clones, the positive clonal cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The resulting chimeric blastocysts formed following the injection are transferred to the culture medium for a short time culture and then transplanted into the fallopian tubes of the recipient mice (white mice) to produce F0 generation chimeric mice (black and white). The F0 generation chimeric mice with correct gene recombination are then selected by extracting the mouse tail genome and detecting by PCR for subsequent breeding and identification. The F1 generation mice are obtained by mating the F0 generation chimeric mice with wildtype mice. Stable gene recombination positive F1 heterozygous mice are selected by extracting rat tail genome and PCR detection. Next, the F1 heterozygous mice are mated to each other to obtain genetically recombinant positive F2 generation homozygous mice. In addition, the F1 heterozygous mice can also be mated with Flp or Cre mice to remove the positive clone screening marker gene (e.g., neo), and then the CD28 gene humanized homozygous mice can be obtained by mating these mice with each other. The methods of genotyping and using the F1 heterozygous mice or F2 homozygous mice are similar to the methods as described in the examples above.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified, non-human mammal whose genome comprises a nucleic acid sequence encoding a chimeric CD28 at an endogenous CD28 gene locus, wherein the chimeric CD28 comprises a humanized CD28 extracellular region and an endogenous CD28 cytoplasmic region, and the nucleic acid sequence encoding the chimeric CD28 is operably linked to an endogenous CD28 promoter, wherein the mammal is homozygous with respect to the nucleic acid sequence encoding the chimeric CD28 and expresses the chimeric CD28.

2. The mammal of claim 1, wherein the mammal is a rodent.

3. The mammal of claim 1, wherein the mammal is a mouse.

4. The mammal of claim 1, wherein the genome of the mammal comprises a nucleic acid sequence encoding a portion of an extracellular region of a human CD28 in place of a nucleic acid sequence encoding a corresponding portion of an extracellular region of an endogenous CD28.

5. The mammal of claim 1, wherein the chimeric CD28 comprises a humanized CD28 extracellular region, an endogenous CD28 transmembrane region, and an endogenous CD28 cytoplasmic region.

6. The mammal of claim 1, wherein the mammal further comprises a sequence encoding an additional human or chimeric protein.

7. The mammal of claim 6, wherein the additional human or chimeric protein is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD40, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), Signal regulatory protein α (SIRPα), or TNF Receptor Superfamily Member 4 (OX40).

8. A method of determining effectiveness of an anti-CD28 antibody for treating cancer, comprising:
administering the anti-CD28 antibody to the mammal of claim 1, wherein the mammal has a cancer; and
determining inhibitory effects of the anti-CD28 antibody to the cancer.

9. The method of claim 8, wherein the anti-CD28 antibody is an anti-human CD28 antibody.

10. The mammal of claim 3, wherein the chimeric CD28 comprises an amino acid sequence that is at least 95% identical to SEQ ID NO: 33.

11. The mammal of claim 3, wherein the chimeric CD28 comprises SEQ ID NO: 33.

12. A genetically-modified, non-human mammal whose genome comprises a chimeric CD28 gene at an endogenous CD28 gene locus, wherein the chimeric CD28 gene comprises a nucleic acid sequence encoding a portion of an extracellular region of a human CD28 in place of a nucleic acid sequence encoding a corresponding portion of an extracellular region of an endogenous CD28, wherein the chimeric CD28 gene is operably linked to an endogenous CD28 promoter, wherein the mammal expresses a chimeric CD28, and the mammal does not express endogenous CD28, wherein the portion of the extracellular region of the human CD28 comprises at least 50 amino acid residues of the extracellular region of the human CD28.

13. The mammal of claim 12, wherein the portion of the extracellular region of the human CD28 comprises at least 100 amino acid residues of the extracellular region of the human CD28.

14. A genetically-modified rodent whose genome comprises a nucleic acid sequence encoding a humanized CD28 at an endogenous CD28 gene locus, wherein the humanized CD28 comprises a humanized CD28 extracellular region, an endogenous CD28 transmembrane region, and an endogenous CD28 cytoplasmic region, and the nucleic acid sequence encoding the humanized CD28 is operably linked to an endogenous CD28 promoter, wherein the rodent is homozygous with respect to the nucleic acid sequence encoding the humanized CD28 and expresses the humanized CD28.

15. The rodent of claim 14, wherein the rodent is a mouse.

* * * * *

SEQUENCE LISTING

<160> NUMBER OF SEQ ID NOS: 54

<210> SEQ ID NO 1
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 1
ctcggcattc gagcgaaact ggg                                     23

<210> SEQ ID NO 2
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 2
tgccgagttc aactgcgacg ggg                                     23

<210> SEQ ID NO 3
<211> LENGTH: 23
<212> TYPE: DNA
<213> ORGANISM: Artificial Sequence

```
<220> FEATURE:
<223> OTHER INFORMATION: sgRNA target sequence

<400> SEQUENCE: 3
cgctgttcac gcccttgtac agg                                              23

<210> SEQ ID NO 4
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 4
caagggcgtg aacagcgacg tgg                                              23

<210> SEQ ID NO 5
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 5
atccccgtcg cagttgaact cgg                                              23

<210> SEQ ID NO 6
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 6
aaacagtgac gttccgtctc tgg                                              23

<210> SEQ ID NO 7
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 7
cccggaattc ctttgcgaga agg                                              23

<210> SEQ ID NO 8
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 8
gcttgtggta gatagcaacg agg                                              23

<210> SEQ ID NO 9
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 9
cgagcgaaac tggggctgat agg                                              23
```

```
<210> SEQ ID NO 10
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 10
tggaagtctg tgtcgggaat ggg                                             23

<210> SEQ ID NO 11
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 11
cgttgctatc taccacaagc agg                                             23

<210> SEQ ID NO 12
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 12
agcgacgtgg aagtctgtgt cgg                                             23

<210> SEQ ID NO 13
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 13
gactcgatca tctaagctgg tgg                                             23

<210> SEQ ID NO 14
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 14
caaattcgcc tctgatgtac agg                                             23

<210> SEQ ID NO 15
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 15
caagactcga tcatctaagc tgg                                             23

<210> SEQ ID NO 16
<211> LENGTH: 23
<212> TYPE: DNA
<213> ORGANISM: Artificial Sequence
<220> FEATURE:
<223> OTHER INFORMATION: sgRNA target sequence
```

```
<400> SEQUENCE: 16
gatgatcgag tcttgctctt tgg                                              23

<210> SEQ ID NO 17
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 17
agtcatctcc taagctgttt tgg                                              23

<210> SEQ ID NO 18
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 18
aaacacaaca tgtgggttaa agg                                              23

<210> SEQ ID NO 19
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 19
atttctgtcc tgtacatcag agg                                              23

<210> SEQ ID NO 20
<211> LENGTH: 23
<212> TYPE: DNA
<213> ORGANISM: Artificial Sequence
<220> FEATURE:
<223> OTHER INFORMATION: sgRNA target sequence

<400> SEQUENCE: 20
ctctgaaaaa cacaacatgt ggg                                              23

<210> SEQ ID NO 21
<211> LENGTH: 15
<212> TYPE: DNA
<213> ORGANISM: Artificial Sequence
<220> FEATURE:
<223> OTHER INFORMATION: sgRNA sequence

<400> SEQUENCE: 21
gcgtgaacag cgacg                                                       15

<210> SEQ ID NO 22
<211> LENGTH: 15
<212> TYPE: DNA
<213> ORGANISM: Artificial Sequence
<220> FEATURE:
<223> OTHER INFORMATION: sgRNA sequence

<400> SEQUENCE: 22
cgtcgctgtt cacgc                                                       15

<210> SEQ ID NO 23
```

```
<211> LENGTH: 18
<212> TYPE: DNA
<213> ORGANISM: Artificial Sequence
<220> FEATURE:
<223> OTHER INFORMATION: sgRNA sequence

<400> SEQUENCE: 23
tcatctccta agctgttt                                                       18

<210> SEQ ID NO 24
<211> LENGTH: 18
<212> TYPE: DNA
<213> ORGANISM: Artificial Sequence
<220> FEATURE:
<223> OTHER INFORMATION: sgRNA sequence

<400> SEQUENCE: 24
aaacagctta ggagatga                                                       18

<210> SEQ ID NO 25
<211> LENGTH: 132
<212> TYPE: DNA
<213> ORGANISM: Artificial Sequence
<220> FEATURE:
<223> OTHER INFORMATION: Synthesized sequence

<400> SEQUENCE: 25
gaattctaat acgactcact ataggggtc ttcgagaaga cctgttttag agctagaaat          60
agcaagttaa ataaggcta gtccgttatc aacttgaaaa agtggcaccg agtcggtgct         120
tttaaaggat cc                                                            132

<210> SEQ ID NO 26
<211> LENGTH: 4317
<212> TYPE: DNA
<213> ORGANISM: Mus musculus

<400> SEQUENCE: 26
agaccttggc agatgtgact tcagttcaca ccacactctg ccttgctcac agaggagggg         60
ctgcagccct ggccctcatc agaacaatga cactcaggct gctgttcttg gctctcaact        120
tcttctcagt tcaagtaaca gaaaacaaga ttttggtaaa gcagtcgccc ctgcttgtgg        180
tagatagcaa cgaggtcagc ctcagctgca ggtattccta caaccttctc gcaaaggaat        240
tccgggcatc cctgtacaag ggcgtgaaca gcgacgtgga agtctgtgtc gggaatggga        300
attttaccta tcagcccag tttcgctcga atgccgagtt caactgcgac ggggatttcg        360
acaacgaaac agtgacgttc cgtctctgga atctgcacgt caatcacaca gatatttact        420
tctgcaaaat tgagttcatg taccctccgc cttacctaga caacgagagg agcaatggaa        480
ctattattca cataaaagag aaacatcttt gtcatactca gtcatctcct aagctgtttt        540
gggcactggt cgtggttgct ggagtcctgt tttgttatgg cttgctagtg acagtggctc        600
tttgtgttat ctggacaaat agtagaagga acagactcct tcaaagtgac tacatgaaca        660
tgactccccg gaggcctggg ctcactcgaa agccttacca gccctacgcc cctgccagag        720
actttgcagc gtaccgcccc tgacaggac ccctatccag aagcccgccg gctggtaccc        780
gtctacctgc tcatcatcac tgctctggat aggaaaggac agcctcatct tcagccggcc        840
actttggacc tctactgggc caccaatgcc aactatttta gagtgtctag atctaacatc        900
atgatcatct tgagactctg gaatgaatga cagaagcttc tatggcagga taaagtctgt        960
gtggcttgac ccaaactcaa gcttaataca tttattgact tgattgggga agttagagta       1020
```

```
gagcaatcaa aaagatcatt cattcagcct tgggaagtca atttgcaggc tcctggatga    1080
gccctgcccc gttttcactt gccagcacat ttcagtcatg tggtgtgata gccaaagatg    1140
ttttggacag agaagaaagg atagaaaaac cttctctttg gctaagttgg tgtttggggt    1200
ggggataggt tagagtatag tacttaacta tttgaaaaat aatgaaaaca cttttttcac    1260
tcatgaaatg agccacttag ctcctaaata gtgttttcct gttagtttag aaagttgtgg    1320 acatatttt ttaatgattt ctgaccattt ttaatcacat tgactcatgg aatgccctca    1380
aagcaccccc cagtgcttct ttcctcattc ccggtcatgg gaactcagta ttattaatag    1440
tcacaacatg atttcagaac tagatagccc tcccacacca agaagaatgt gagaggaagt    1500
aaggtcactt tatgtaaaaa aaaaaaaaaa caaacgcgta cacatatgta tgtatacata    1560 cataccctatg tgcacacaca cacacatata catacacaca aaatgctatg aagagttatc    1620
tgtttagtag cctgttatag tcaaatcatt ttaagtttca acttcttaca gttgggccac    1680
ttgttgtcct ttgtggatgg atatctgaaa ttgtgtctat atattgctag tcatgatact    1740
gtgaacaaaa agggtagtgt tagtatttgt cagggtggta aggatgcatt ccaggaagct    1800
tcctctgagg aagggaatga ggtcattctt gccatgtatg aaagacatag atgttttcca    1860
gaaggcacca ttgggagccc cagtataagt tcctttagac tctacagttt agagggattt    1920
tatatgtcct aggactcagg actccagaac tttgtgggct cagctgcttc ataccatggg    1980
gatacattga catgaacaat tattttggaa tgtgtcttta gggacgacat caaagttctc    2040
aagtacctac aagacctgat actggaatga aggtggactt tctttttgc ttccagttcg    2100 gatcaactgg aatgtatctg ggaccttga agaacggctg tccagctgtc ttcaccattt    2160
gtatagtgct ttgaattatt cagaggtttt aaagtcagga agacctggtt taaaaaacat    2220
ttcattatga gttaaatggc ctcaggcaag tcactgttca tccaagtcta tgactcctca    2280
actgtaagat ggccacactg aaacttgcta agatcctctg gcctctgcct cccaagagtt    2340
gggatttcag gagtgcacaa tcatgaccca aactcgtgat aatctctcag cttcaataac    2400
tttccagcta attggaatat cctgtaatca aacatgaggc atttcccctc cccccactgt    2460
ttttgtgtat aaagagatct ttaaactttt tttttaatat gagggggtaag aaaagatagg    2520 aatctttttaa ttctagacag aagatattgt gctttggttt tttttttttt taatggcttc    2580
tattctgtgc ttttaattaa accagagaag gccaagatta gccctacttg tgtgataaaa    2640
gaatgctggc ccttgtgatt gcagtcagcc tcttgacaca tagagttctt gaatctaagt    2700
tataaaatta tatttgaaaa tgacagagct ggagaattta tagaaagggt catagcaaat    2760
aacaaaccat ttttttttaa acggaaagat ttggtctttg gcaatcaata actttgtttt    2820
ctaactggaa aaggaggttt actggagatg aatcacacct gaaagttttc atacctcctc    2880
tgaacacaac cgaaacatag gtgtccaaag cctttcgctc tcggtatgaa ccaacaggcg    2940
ggttaaaaac actgggtcag agtaaagctt ttgcagtttc agatgtagtg tgtatgaaga    3000
aaactatgtc acttgctgct attattgtaa gagtctaaga actaaaggtg tgcctgtaat    3060
ttctaattat gagctcacct atttggtacc gagcatgcca attttaaaga gacccggtgt    3120
accttatagc tacatccaat gataaaatta ccacactagc acatgcctgt gtttaaactc    3180
gtgctttaat gttttttctta gggcaggtat gcaccccctt tgcagtgagt tgggagagat    3240
tttgaaaaag tgtatgacaa acattttaa caccctttggt ttcctctctc tgtgtctctt    3300
tgtctctgtc tctctctttc tctcctgtgc atatgtctcc cctccctcac ttctctgtct    3360
```

-continued

```
cttcctctct ccctctctct gtctttctct gtgtgtctct ctgtctctgt gtatctctct    3420
gtctgtctct ttctctgcag attttcaaaa cgttgttttt ctatggaaga aatacaagct    3480
gtggttggtt tgctacgagt cagtagcagt ttatcagtag gccaatgttt tatctcttgg    3540
agatttcagt ctgggtttac ccaatgtatt ctctgtaatg tgactgctgg ggacagatat    3600
aacttgattg agccttcaaa tcatttaggt cttcaatcat ttagtcaacg gagtgagcca    3660
ctaatctgca atggctattt taatatgcat actgatggtc aaatggatgt ctgatctctc    3720
atcccagctt tctgtactac catatgggaa ctatatgtaa cttgtatact tacctgaata    3780
tgttaaattc aactacatgg taagatggac cagaaattgc aatgttcatg tccatatagc    3840
caccattaac ccaagttaag cacagtagtg tgggttctct caggacttgt gaatgagttt    3900
atgctctcta caaagacagg tgaagcttaa atctctcttg cactgctatg tttatgcaaa    3960
tatcaagatt gtttctgtac cagggactta acacattcta ttcatactat tttccctgtc    4020
tacaatgtta tttcatagat atctacttgg tttgctctta cttccttgac atatttgccc    4080
aaatgccacc ttcaactgta gttaattacc tgtacaacct gtctccatgc cttgttttat    4140
tttctctata actctactaa taggtatttt tcttatttat tggtttattg cctgttttt     4200 ttcctaaatc tacaccggat ctccaaaggg aaagaactcc atttgctttg attttattgc    4260
tgtatcccca gtgcctagaa taatgcttag cctgcaataa atatttattc attgact       4317
```

<210> SEQ ID NO 27
<211> LENGTH: 218
<212> TYPE: PRT
<213> ORGANISM: Mus musculus

<400> SEQUENCE: 27

```
Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
            20                  25                  30

Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Pro Tyr Leu Asp Asn Glu Arg
        115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
            180                 185                 190

Thr Pro Arg Arg Pro Gly Leu Thr Arg Lys Pro Tyr Gln Pro Tyr Ala
        195                 200                 205
```

Pro Ala Arg Asp Phe Ala Ala Tyr Arg Pro
    210                 215

<210> SEQ ID NO 28
<211> LENGTH: 4900
<212> TYPE: DNA
<213> ORGANISM: Homo sapiens

<400> SEQUENCE: 28

| | | | | | |
|---|---|---|---|---|---|
| taaagtcatc | aaaacaacgt | tatatcctgt | gtgaaatgct | gcagtcagga | tgccttgtgg | 60 |
| tttgagtgcc | ttgatcatgt | gccctaaggg | gatggtggcg | gtggtggtgg | ccgtggatga | 120 |
| cggagactct | caggccttgg | caggtgcgtc | tttcagttcc | cctcacactt | cgggttcctc | 180 |
| ggggaggagg | ggctggaacc | ctagcccatc | gtcaggacaa | agatgctcag | gctgctcttg | 240 |
| gctctcaact | tattcccttc | aattcaagta | acaggaaaca | agattttggt | gaagcagtcg | 300 |
| cccatgcttg | tagcgtacga | caatgcggtc | aaccttagct | gcaagtattc | ctacaatctc | 360 |
| ttctcaaggg | agttccgggc | atcccttcac | aaaggactgg | atagtgctgt | ggaagtctgt | 420 |
| gttgtatatg | ggaattactc | ccagcagctt | caggtttact | caaaaacggg | gttcaactgt | 480 |
| gatgggaaat | tggcaatgga | atcagtgaca | ttctacctcc | agaatttgta | tgttaaccaa | 540 |
| acagatattt | acttctgcaa | aattgaagtt | atgtatcctc | ctccttacct | agacaatgag | 600 |
| aagagcaatg | gaaccattat | ccatgtgaaa | gggaaacacc | tttgtccaag | tcccctattt | 660 |
| cccggacctt | ctaagccctt | tgggtgctg | gtggtggttg | gtggagtcct | ggcttgctat | 720 |
| agcttgctag | taacagtggc | ctttattatt | ttctgggtga | ggagtaagag | gagcaggctc | 780 |
| ctgcacagtg | actacatgaa | catgactccc | cgccgccccg | ggcccacccg | caagcattac | 840 |
| cagccctatg | ccccaccacg | cgacttcgca | gcctatcgct | cctgacacgg | acgcctatcc | 900 |
| agaagccagc | cggctggcag | cccccatctg | ctcaatatca | ctgctctgga | taggaaatga | 960 |
| ccgccatctc | cagccggcca | cctcaggccc | ctgttgggcc | accaatgcca | atttttctcg | 1020 |
| agtgactaga | ccaaatatca | agatcatttt | gagactctga | aatgaagtaa | aagagatttc | 1080 |
| ctgtgacagg | ccaagtctta | cagtgccatg | gcccacattc | caacttacca | tgtacttagt | 1140 |
| gacttgactg | agaagttagg | gtagaaaaca | aaaagggagt | ggattctggg | agcctcttcc | 1200 |
| ctttctcact | cacctgcaca | tctcagtcaa | gcaaagtgtg | gtatccacag | acattttagt | 1260 |
| tgcagaagaa | aggctaggaa | atcattcctt | ttggttaaat | gggtgtttaa | tcttttggtt | 1320 |
| agtgggttaa | acggggtaag | ttagagtagg | gggagggata | ggaagacata | tttaaaaacc | 1380 |
| attaaaacac | tgtctcccac | tcatgaaatg | agccacgtag | ttcctattta | atgctgtttt | 1440 |
| cctttagttt | agaaatacat | agacattgtc | ttttatgaat | tctgatcata | tttagtcatt | 1500 |
| ttgaccaaat | gagggatttg | gtcaaatgag | ggattccctc | aaagcaatat | caggtaaacc | 1560 |
| aagttgcttt | cctcactccc | tgtcatgaga | cttcagtgtt | aatgttcaca | atatactttc | 1620 |
| gaaagaataa | aatagttctc | ctacatgaag | aaagaatatg | tcaggaaata | aggtcacttt | 1680 |
| atgtcaaaat | tatttgagta | ctatgggacc | tggcgcagtg | gctcatgctt | gtaatcccag | 1740 |
| cactttggga | ggccgaggtg | ggcagatcac | ttgagatcag | gaccagcctg | gtcaagatgg | 1800 |
| tgaaactccg | tctgtactaa | aaatacaaaa | tttagcttgg | cctggtggca | ggcacctgta | 1860 |
| atcccagctg | cccaagaggc | tgaggcatga | gaatcgcttg | aacctggcag | gcggaggttg | 1920 |
| cagtgagccg | agatagtgcc | acagctctcc | agcctgggcg | acagagtgag | actccatctc | 1980 |
| aaacaacaac | aacaacaaca | acaacaacaa | caaaccacaa | aattatttga | gtactgtgaa | 2040 |

```
ggattatttg tctaacagtt cattccaatc agaccaggta ggagctttcc tgtttcatat      2100
gtttcagggt tgcacagttg gtctctttaa tgtcggtgtg gagatccaaa gtgggttgtg      2160
gaaagagcgt ccataggaga agtgagaata ctgtgaaaaa gggatgttag cattcattag      2220
agtatgagga tgagtcccaa gaaggttctt tggaaggagg acgaatagaa tggagtaatg      2280
aaattcttgc catgtgctga ggagatagcc agcattaggt gacaatcttc cagaagtggt      2340
caggcagaag gtgccctggt gagagctcct ttacagggac tttatgtggt ttagggctca      2400
gagctccaaa actctgggct cagctgctcc tgtaccttgg aggtccattc acatgggaaa      2460
gtatttggga atgtgtcttt tgaagagagc atcagagttc ttaagggact gggtaaggcc      2520
tgaccctgaa atgaccatgg atattttcct acctacagtt tgagtcaact agaatatgcc      2580
tggggacctt gaagaatggc ccttcagtgg ccctcaccat ttgttcatgc ttcagttaat      2640
tcaggtgttg aaggagctta ggttttagag gcacgtagac ttggttcaag tctcgttagt      2700
agttgaatag cctcaggcaa gtcactgccc acctaagatg atggttcttc aactataaaa      2760
tggagataat ggttacaaat gtctcttcct atagtataat ctccataagg gcatggccca      2820
agtctgtctt tgactctgcc tatccctgac atttagtagc atgcccgaca tacaatgtta      2880
gctattggta ttattgccat atagataaat tatgtataaa aattaaactg ggcaatagcc      2940
taagaagggg ggaatattgt aacacaaatt taaacccact acgcagggat gaggtgctat      3000
aatatgagga ccttttaact tccatcattt tcctgtttct tgaaatagtt tatcttgtaa      3060
tgaaatataa ggcacctccc acttttatgt atagaaagag gtcttttaat tttttttaa       3120 tgtgagaagg aagggaggag taggaatctt gagattccag atcgaaaata ctgtactttg      3180
gttgattttt aagtgggctt ccattccatg gatttaatca gtcccaagaa gatcaaactc      3240
agcagtactt gggtgctgaa gaactgttgg atttaccctg gcacgtgtgc cacttgccag      3300
cttcttgggc acacagagtt cttcaatcca agttatcaga ttgtatttga aaatgacaga      3360
gctggagagt ttttgaaat ggcagtggca aataaataaa tactttttt taaatggaaa       3420 gacttgatct atggtaataa atgattttgt tttctgactg gaaaaatagg cctactaaag      3480
atgaatcaca cttgagatgt ttcttactca ctctgcacag aaacaaagaa gaaatgttat      3540
acagggaagt ccgttttcac tattagtatg aaccaagaaa tggttcaaaa acagtggtag      3600
gagcaatgct ttcatagttt cagatatggt agttatgaag aaaacaatgt catttgctgc      3660
tattattgta agagtcttat aattaatggt actcctataa tttttgattg tgagctcacc      3720
tatttgggtt aagcatgcca atttaaagag accaagtgta tgtacattat gttctacata      3780
ttcagtgata aaattactaa actactatat gtctgcttta aatttgtact ttaatattgt      3840
cttttggtat taagaaagat atgctttcag aatagatatg cttcgctttg gcaaggaatt      3900
tggatagaac ttgctattta aaagaggtgt ggggtaaatc cttgtataaa tctccagttt      3960 agccttttt gaaaaagcta gactttcaaa tactaatttc acttcaagca gggtacgttt       4020
ctggtttgtt tgcttgactt cagtcacaat ttcttatcag accaatggct gacctctttg      4080
agatgtcagg ctaggcttac ctatgtgttc tgtgtcatgt gaatgctgag aagtttgaca      4140
gagatccaac ttcagcctt g accccatcag tccctcgggt taactaactg agccaccggt     4200
cctcatggct atttaatga gggtattgat ggttaaatgc atgtctgatc ccttatccca       4260
gccatttgca ctgccagctg gaactatac cagacctgga tactgatccc aaagtgttaa       4320
attcaactac atgctggaga ttagagatgg tgccaataaa ggacccagaa ccaggatctt      4380
gattgctata gacttattaa taatccaggt caaagagagt gacacacact ctctcaagac      4440
```

```
ctgggggtgag ggagtctgtg ttatctgcaa ggccatttga ggctcagaaa gtctctcttt    4500
cctatagata tatgcatact ttctgacata taggaatgta tcaggaatac tcaaccatca    4560
caggcatgtt cctacctcag ggcctttaca tgtcctgttt actctgtcta gaatgtcctt    4620
ctgtagatga cctggcttgc ctcgtcaccc ttcaggtcct tgctcaagtg tcatcttctc    4680
ccctagttaa actaccccac accctgtctg ctttccttgc ttattttcct ccatagcatt    4740
ttaccatctc ttacattaga cattttctt atttatttgt agtttataag cttcatgagg    4800
caagtaactt tgctttgttt cttgctgtat ctccagtgcc cagagcagtg cctggtatat    4860
aataaatatt tattgactga gtgaaaaaaa aaaaaaaaa                           4900
```

<210> SEQ ID NO 29
<211> LENGTH: 220
<212> TYPE: PRT
<213> ORGANISM: Homo sapiens

<400> SEQUENCE: 29

```
Met Leu Arg Leu Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220
```

<210> SEQ ID NO 30
<211> LENGTH: 3432
<212> TYPE: DNA
<213> ORGANISM: Artificial Sequence
<220> FEATURE:
<223> OTHER INFORMATION: Homo sapiens and Mus musculus

<400> SEQUENCE: 30

```
aaacttgaga actttcagtg tagtcatcat tccaagaaga gctattaata tatcttttc      60
```

-continued

```
tgccaaggga ctaactttgt tggaggtctg ttcagttggc taattaattc actttgattt    120
cagggcaatg gaattattat tcttatgctc ctaactaaat gttttttttcc cttcagaaaa    180 caagattttg gtaaagcagt cgcccatgct tgtagcgtac gacaatgcgg tcaaccttag    240
ctgcaagtat tcctacaatc tcttctcaag ggagttccgg gcatcccttc acaaaggact    300
ggatagtgct gtggaagtct gtgttgtata tgggaattac tcccagcagc ttcaggttta    360
ctcaaaaacg gggttcaact gtgatgggaa attgggcaat gaatcagtga cattctacct    420
ccagaatttg tatgttaacc aaacagatat ttacttctgc aaaattgaag ttatgtatcc    480
tcctccttac ctagacaatg agaagagcaa tggaaccatt atccatgtga aggtaacat     540 acaactttac cagtgtacca ccctaaagta atggttttca aatgcagtcc tgaaaactgg    600
gttgtggtca gtggtggggt tgaataaggc ctaagtgatt tgatactaac aaagacaaat    660
aatgttttca gaaaaatttt tccctttact gtagaggaga ttcaaggtta tattttgaat    720
atctttattt tccttttgctg acattgagcg ggagagtaag tgatgaagtt accgcatgtg    780
ggaacagatc attttttctcc attccagtgg atcatggcag aaaagaggtt accattaaaa    840
tgtaagccca ggtgccctca agtaacagct gggtctaatg ggttaagact caggaagact    900
cacttctatt tctaattaat tcttttttttg tgctccataa tcttcctctg taaaagtacc    960
tttccatttt cttttttcctt ccttcctttcc ttccttcctt ccttcctttcc ttttctttttc   1020 tttttctttt tcttttttttt tgagacggac tctcgctctg tcgcccaggc tggagtgcag   1080
tggcgggatc tcagttcact gcaagctctg cctcccgggt tcacgtcatt ctcctgcctc   1140
agcctcccga tcagctggga ctacagggcc cgccaccacg cctggcttat ttttttgtata   1200 tttatttatt tattttatttt aattaattaa ttttttttttt tgagagggag tcttgctctg   1260
tcgcccaggc tggaatgcgg tggcgcgatc tcggctcact gcaagctccg cctcccaggt   1320
tcatgccatt ctcctgcctc agcctcctga gtagctggga ctacaggtac ctgccaccat   1380
gcccggctaa ttttttgtat ttttagtaga cagggtttca ccttgttagc caggatggtc   1440
tcgatttcct gacctcgtga cccgcccgtg ttggcctccc aaagtgctgg gattacaggc   1500
gtgagccacc gcgcccagcc attttttgta cttttagtag agacggggtt tcaccgtgtt   1560
agcaaggatg gtctcaatct cctgacctcg tgatctgccc acctgggcct cccaaagtgc   1620
tgtgattaca ggcgtaagcc accgcgccca gcccgtacct ttccattttc taaaatatac   1680
aaagaatgct ggactagaaa ccgggggaca taaaatttgc tattaatcaa ctgtgtgatc   1740
ttggataagt cacctaactt tttcatagtc aaaaactcag tacaactgtt aagcagtatt   1800
tgtgaattag tgaaaataag tctactgaac ttttgttgat gttatgttct gcctaaatgt   1860
tagggagaaa aatcatgatt ccccaactca gaagaataca gtattggtag caacaagtaa   1920
agtttgattt tttggtatac tttgtggata tatcatagct tttcattttt gtggaatgat   1980
aataagaaac acatatgttc agttttgtac tgaatcctag cataatgcca atgaatggtt   2040
tttcttcaat gctggaacag agccatgctg atgaaaaata ggatactaaa taaggaaaga   2100
attgttaatg tggcagataa gcttttgtgt tctggcaaaa tagagacaat taatgtgtga   2160 atatttttgtt tgctgagtcc tatttagatt tctaatatct gtaatatcca aacagaatat   2220
tttaattgta tcaagtcaaa ggttaaaaaa ttatgctatt ttgcttgtag ctaagagtga   2280
aatatttttt cctatatgaa aggcatgcta ctttaggata gtattttata tatatgtata   2340
cacacatata cacatatcat ttatgttaga actgagaagg acaccaatga tcctgtactt   2400
agtaattttc aatcctatct gtatattata aatctgagta ggttttaaaa gaaataccaa   2460
```

```
tgcctagttc cagccctgag attctgatgt aattgatatg ggttgaggaa ggggtgctgg    2520
acatcagtat attttcaaac tttctcggat aatttattgt gcagctagga tggaaaatca    2580
atggactaga ggattttggg tatgctttct agttctaatt ttctctaatt ttgaatagaa    2640
ttctataggt tccttctcat cccctttga ttcctaaaga tacaaagtga tttgtttgtc    2700
attatataat ctatgagaca gggttggaac tagaaattta tcctctgatt agcagtccag    2760
tgttctgact gccatattag gctgatgatt ttcttaaggc ttgaaaacat gcatattatt    2820
taacttattc caaggatgca gtttagggtc tagattaact atcttctgat gggagaaacg    2880
gataaagtta ggttaaggcc attggaagtc accgttttga atcacacagt agaatccaca    2940
aagtcaagtg aatacaagtc taccagtgta ccatcctaac gtaatggctt tcaactgtgg    3000
tcgtgaaaac tgaccagatc atggtcagtg gtggggttgg gtaagtctca agaggaaat    3060 ctattcactc taagctggtg atatgtttaa tatttttatt tctttcacat ttttctctga    3120
tgttcacaag gaaggaaatg cactcaattg ctattcctgt atcatttaat ccactctatt    3180
ttgtttttca gggaaacacc tttgtccaag tcccctattt cccggaccttt ctaagctgtt    3240 ttgggcactg gtcgtggttg ctggagtcct gttttgttat ggcttgctag tgacagtggc    3300
tctttgtgtt atctgggtaa gaggagcaac attgctttta tgtaacttct ctgcgcctgc    3360
cctctgacta tattaagact ctggcctgta tcttttctac gttaaagcaa atgacgcttt    3420
tcagtctgtc ca                                                        3432

<210> SEQ ID NO 31
<211> LENGTH: 666
<212> TYPE: DNA
<213> ORGANISM: Artificial Sequence
<220> FEATURE:
<223> OTHER INFORMATION: Homo sapiens & Mus musculus

<400> SEQUENCE: 31
atgacactca ggctgctgtt cttggctctc aacttcttct cagttcaagt aacagaaaac     60
aagattttgg taaagcagtc gcccatgctt gtagcgtacg acaatgcggt caaccttagc    120
tgcaagtatt cctacaatct cttctcaagg gagttccggg catcccttca caaaggactg    180
gatagtgctg tggaagtctg tgttgtatat gggaattact cccagcagct tcaggtttac    240
tcaaaaacgg ggttcaactg tgatgggaaa ttgggcaatg aatcagtgac attctacctc    300
cagaatttgt atgttaacca aacagatatt tacttctgca aaattgaagt tatgtatcct    360
cctccttacc tagacaatga aagagcaat ggaaccatta tccatgtgaa agggaaacac    420
ctttgtccaa gtcccctatt tcccggacct tctaagctgt tttgggcact ggtcgtggtt    480
gctggagtcc tgttttgtta tggcttgcta gtgacagtgg ctctttgtgt tatctggaca    540
aatagtagaa ggaacagact ccttcaaagt gactacatga acatgactcc ccggaggcct    600
gggctcactc gaaagcctta ccagccctac gcccctgcca gagactttgc agcgtaccgc    660
ccctga                                                              666

<210> SEQ ID NO 32
<211> LENGTH: 4326
<212> TYPE: DNA
<213> ORGANISM: Artificial Sequence
<220> FEATURE:
<223> OTHER INFORMATION: Homo sapiens and Mus musculus

<400> SEQUENCE: 32
```

-continued

```
agaccttggc agatgtgact tcagttcaca ccacactctg ccttgctcac agaggagggg      60
ctgcagccct ggccctcatc agaacaatga cactcaggct gctgttcttg gctctcaact     120
tcttctcagt tcaagtaaca gaaaacaaga ttttggtaaa gcagtcgccc atgcttgtag     180
cgtacgacaa tgcggtcaac cttagctgca agtattccta caatctcttc tcaagggagt     240
tccgggcatc ccttcacaaa ggactggata gtgctgtgga agtctgtgtt gtatatggga     300
attactccca gcagcttcag gtttactcaa aaacgggggtt caactgtgat gggaaattgg    360
gcaatgaatc agtgacattc tacctccaga atttgtatgt taaccaaaca gatatttact     420
tctgcaaaat tgaagttatg tatcctcctc cttacctaga caatgagaag agcaatggaa     480
ccattatcca tgtgaaaggg aaacaccttt gtccaagtcc cctatttccc ggaccttcta     540
agctgttttg ggcactggtc gtggttgctg gagtcctgtt ttgttatggc ttgctagtga     600
cagtggctct ttgtgttatc tggacaaata gtagaaggaa cagactcctt caaagtgact     660
acatgaacat gactccccgg aggcctgggc tcactcgaaa gccttaccag ccctacgccc     720
ctgccagaga ctttgcagcg taccgccccct gacaggggacc cctatccaga agcccgccgg    780
ctggtacccg tctacctgct catcatcact gctctggata ggaaaggaca gcctcatctt     840
cagccggcca ctttggaccct ctactgggcc accaatgcca actattttag agtgtctaga    900
tctaacatca tgatcatctt gagactctgg aatgaatgac agaagcttct atggcaggat     960
aaagtctgtg tggcttgacc caaactcaag cttaatacat ttattgactt gattggggaa    1020
gttagagtag agcaatcaaa aagatcattc attcagcctt gggaagtcaa tttgcaggct    1080
cctggatgag ccctgccccg ttttcacttg ccagcacatt tcagtcatgt ggtgtgatag    1140
ccaaagatgt tttggacaga gaagaaagga tagaaaaacc ttctctttgg ctaagttggt    1200
gtttggggtg gggataggtt agagtatagt acttaactat ttgaaaaata atgaaaacac    1260
ttttttcact catgaaatga gccacttagc tcctaaatag tgttttcctg ttagtttaga    1320
aagttgtgga catatttttt taatgatttc tgaccatttt taatcacatt gactcatgga    1380
atggcctcaa agcaccccc agtgcttctt tcctcattcc cggtcatggg aactcagtat    1440
tattaatagt cacaacatga tttcagaact agatagccct cccacaccaa gaagaatgtg    1500
agaggaagta aggtcacttt atgtaaaaaa aaaaaaaaac aaacgcgtac acatatgtat    1560
gtatacatac atacctatgt gcacacacac acacatatac atacacacaa aatgctatga    1620
agagttatct gtttagtagc ctgttatagt caaatcattt taagtttcaa cttcttacag    1680
ttgggccact tgttgtcctt tgtggatgga tatctgaaat tgtgtctata tattgctagt    1740
catgatactg tgaacaaaaa gggtagtgtt agtatttgtc agggtggtaa ggatgcattc    1800
caggaagctt cctctgagga agggaatgag gtcattcttg ccatgtatga aagacataga    1860
tgttttccag aaggcaccat tgggagcccc agtataagtt cctttagact ctacagttta    1920
gagggatttt atatgtccta ggactcagga ctccagaact ttgtgggctc agctgcttca    1980
taccatgggg atacattgac atgaacaatt attttggaat gtgtctttag ggacgacatc    2040
aaagttctca gtacctaca agacctgata ctggaatgaa ggtggacttt cttttttgct    2100
tccagttcgg atcaactgga atgtatctgg ggaccttgaa gaacggctgt ccagctgtct    2160
tcaccatttg tatagtgctt tgaattattc agaggtttta aagtcaggaa gacctggttt    2220
aaaaaacatt tcattatgag ttaaatggcc tcaggcaagt cactgttcat ccaagtctat    2280
gactcctcaa ctgtaagatg gccacactga aacttgctaa gatcctctgg cctctgcctc    2340
ccaagagttg ggatttcagg agtgcacaat catgacccaa actcgtgata atctctcagc    2400
```

```
ttcaataact ttccagctaa ttggaatatc ctgtaatcaa acatgaggca tttcccctcc    2460
ccccactgtt tttgtgtata aagagatctt taaactttt ttttaatatg aggggtaaga    2520
aaagatagga atcttttaat tctagacaga agatattgtg ctttggtttt ttttttttt    2580 aatggcttct attctgtgct tttaattaaa ccagagaagg ccaagattag ccctacttgt    2640
gtgataaaag aatgctggcc cttgtgattg cagtcagcct cttgacacat agagttcttg    2700
aatctaagtt ataaaattat atttgaaaat gacagagctg gagaatttat agaaagggtc    2760
atagcaaata acaaccatt ttttttaaa cggaaagatt tggtctttgg caatcaataa    2820
ctttgttttc taactggaaa aggaggttta ctggagatga atcacacctg aaagttttca    2880
tacctcctct gaacacaacc gaaacatagg tgtccaaagc ctttcgctct cggtatgaac    2940
caacaggcgg gttaaaaaca ctgggtcaga gtaaagcttt tgcagtttca gatgtagtgt    3000
gtatgaagaa aactatgtca cttgctgcta ttattgtaag agtctaagaa ctaaaggtgt    3060
gcctgtaatt tctaattatg agctcaccta tttggtaccg agcatgccaa ttttaaagag    3120
acccggtgta ccttatagct acatccaatg ataaaattac cacactagca catgcctgtg    3180
tttaaactcg tgctttaatg ttttttcttag ggcaggtatg cacccccttt gcagtgagtt    3240
gggagagatt ttgaaaaagt gtatgacaaa cattttaac acctttggtt tcctctctct    3300
gtgtctcttt gtctctgtct ctctctttct tcctgtgca tatgtctccc ctccctcact    3360
tctctgtctc ttcctctctc cctctctctg tctttctctg tgtgtctctc tgtctctgtg    3420
tatctctctg tctgtctctt tctctgcaga ttttcaaaac gttgtttttc tatggaagaa    3480
atacaagctg tggttggttt gctacgagtc agtagcagtt tatcagtagg ccaatgtttt    3540
atctcttgga gatttcagtc tgggtttacc caatgtattc tctgtaatgt gactgctggg    3600
gacagatata acttgattga gccttcaaat catttaggtc ttcaatcatt tagtcaacgg    3660
agtgagccac taatctgcaa tggctatttt aatatgcata ctgatggtca aatggatgtc    3720
tgatctctca tcccagcttt ctgtactacc atatgggaac tatatgtaac ttgtatactt    3780
acctgaatat gttaaattca actacatggt aagatggacc agaaattgca atgttcatgt    3840
ccatatagcc accattaacc caagttaagc acagtagtgt gggttctctc aggacttgtg    3900
aatgagttta tgctctctac aaagacaggt gaagcttaaa tctctcttgc actgctatgt    3960
ttatgcaaat atcaagattg tttctgtacc agggacttaa cacattctat tcatactatt    4020
ttccctgtct acaatgttat ttcatagata tctacttggt ttgctcttac ttccttgaca    4080
tatttgccca aatgccacct tcaactgtag ttaattacct gtacaacctg tctccatgcc    4140
ttgttttatt ttctctataa ctctactaat aggtattttt cttatttatt ggtttattgc    4200 ctgtttttt tcctaaatct acaccggatc tccaaaggga aagaactcca tttgctttga    4260
ttttattgct gtatccccag tgcctagaat aatgcttagc ctgcaataaa tatttattca    4320
ttgact                                                              4326
```

<210> SEQ ID NO 33
<211> LENGTH: 221
<212> TYPE: PRT
<213> ORGANISM: Artificial Sequence
<220> FEATURE:
<223> OTHER INFORMATION: Homo sapiens and Mus musculus

<400> SEQUENCE: 33

```
Met Thr Leu Arg Leu Leu Phe Leu Ala Leu Asn Phe Phe Ser Val Gln
1               5                   10                  15
```

```
Val Thr Glu Asn Lys Ile Leu Val Lys Gln Ser Pro Met Leu Val Ala
         20                  25                  30

Tyr Asp Asn Ala Val Asn Leu Ser Cys Lys Tyr Ser Tyr Asn Leu Phe
         35                  40                  45

Ser Arg Glu Phe Arg Ala Ser Leu His Lys Gly Leu Asp Ser Ala Val
 50                  55                  60

Glu Val Cys Val Val Tyr Gly Asn Tyr Ser Gln Gln Leu Gln Val Tyr
 65                  70                  75                  80

Ser Lys Thr Gly Phe Asn Cys Asp Gly Lys Leu Gly Asn Glu Ser Val
                 85                  90                  95

Thr Phe Tyr Leu Gln Asn Leu Tyr Val Asn Gln Thr Asp Ile Tyr Phe
                100                 105                 110

Cys Lys Ile Glu Val Met Tyr Pro Pro Pro Tyr Leu Asp Asn Glu Lys
            115                 120                 125

Ser Asn Gly Thr Ile Ile His Val Lys Gly Lys His Leu Cys Pro Ser
130                 135                 140

Pro Leu Phe Pro Gly Pro Ser Lys Leu Phe Trp Ala Leu Val Val Val
145                 150                 155                 160

Ala Gly Val Leu Phe Cys Tyr Gly Leu Leu Val Thr Val Ala Leu Cys
                165                 170                 175

Val Ile Trp Thr Asn Ser Arg Arg Asn Arg Leu Leu Gln Ser Asp Tyr
                180                 185                 190

Met Asn Met Thr Pro Arg Arg Pro Gly Leu Thr Arg Lys Pro Tyr Gln
            195                 200                 205

Pro Tyr Ala Pro Ala Arg Asp Phe Ala Ala Tyr Arg Pro
        210                 215                 220

<210> SEQ ID NO 34
<211> LENGTH: 1330
<212> TYPE: DNA
<213> ORGANISM: Artificial
<220> FEATURE:
<223> OTHER INFORMATION: Mus musculus

<400> SEQUENCE: 34
cggtcagcta tttaggtggt gtagcctttg gtttcagttc tgattttgtt caccatttgc      60
tcaatgtctg tagatgaacc attcatgttt ctagacctca ttcagtcatc tttttctttt    120
taaacaaatg tacagggacg gtgtcccaca cttttaatcc caacactcag gaggcaaagg    180
caggtgaatt agtgagttat aggccagcct ggtctatgta gtagacagcc agtgaatacc    240
tgtttctgtt tctgttttgt tttgtttgtt tagaaaaaaa aaagagagtc aaagacatgg    300
taggcacctg ttaccaagcc tgacctgtgg gtggagggaa agaaccaatc ctacaacttg    360
acctctgacc tccatttgca tgcatgttct ctctctctct ctctctctct ctctctctct    420
ctctctctct cacacacaca catttaaaat gtaatacttt cttttaaaaa aggagtgtac    480
ttctgtattt ctgtgttctg gaaatggggg tgcattggaa acagtacgag ctttgtctcc    540
cttctcccaa aggaactgag agtatagttt tattttcttt gcctttaagg ggagaaattg    600
aattagatgg tatccagagc tttgattgtt gcataaagat agaactcttc ttgctttgag    660
agaataatca tgcaacgttt tgggaggct cttatctgaa tttgctctgg aagagtaatt    720
taagccagcc cttggggcta caaacgtggt gcctttcttt accccttttat tgactgctct    780 tggtttggtc aataagcaaa gtcagaatgt tttaaaactt tgaaatactt ttacaaaaat    840
ctgttgcaga gttgaaaaaa aaatcacttg gacatctgtg tcaggctttc aagaggcctc    900
```

```
caagctgatc agttattcag gaagtcaacc caaggcctga ctaacatcat aggaatctca    960
actggactaa caaaattcta gtgactagct ggggtgctca atgctcacag cagctcacat   1020
ttagctgggg tactcagtgc tcacagcagc tcacattgtg ctgtccaggt ggaagcacgc   1080
tcctgtcttc ccattcagag aaagatgcca gcatcattga aatataaact tgagaacttt   1140
cagtgtagtc atcattccaa gaagagctat taatatatct ttttctgcca agggactaac   1200
tttgttggag gtctgttcag ttggctaatt aattcacttt gatttcaggg caatggaatt   1260
attattctta tgctcctaac taaatgtttt tttcccttca gaaaacaaga ttttggtaaa   1320
gcagtcgccc                                                          1330
```

<210> SEQ ID NO 35
<211> LENGTH: 3027
<212> TYPE: DNA
<213> ORGANISM: Artificial
<220> FEATURE:
<223> OTHER INFORMATION: Homo sapiens

<400> SEQUENCE: 35

```
atgcttgtag cgtacgacaa tgcggtcaac cttagctgca agtattccta caatctcttc     60
tcaagggagt tccgggcatc ccttcacaaa ggactggata gtgctgtgga agtctgtgtt    120
gtatatggga attactccca gcagcttcag gtttactcaa aaacgggggtt caactgtgat    180 gggaaattgg gcaatgaatc agtgacattc tacctccaga atttgtatgt taaccaaaca    240
gatatttact tctgcaaaat tgaagttatg tatcctcctc cttacctaga caatgagaag    300
agcaatggaa ccattatcca tgtgaaaggt aacatacaac tttaccagtg taccaccctat    360 aagtaatggt tttcaaatgc agtcctgaaa actgggttgt ggtcagtggt ggggttgaat    420
aaggcctaag tgatttgata ctaacaaaga caaataatgt tttcagaaaa atttttccct    480
ttactgtaga ggagattcaa ggttatattt tgaatatctt tattttcctt tgctgacatt    540
gagcgggaga gtaagtgatg aagttaccgc atgtgggaac agatcatttt ctccattcc    600 agtggatcat ggcagaaaag aggttaccat taaaatgtaa gcccaggtgc cctcaagtaa    660
cagctgggtc taatgggtta agactcagga agactcactt ctattctaa ttaattcttt    720 ttttgtgctc cataatcttc ctctgtaaaa gtaccttttcc attttctttt tccttccttc    780
cttccttcct tccttccttc cttcctttttc ttttctttt cttttctttt tttttgaga    840 cggactctcg ctctgtcgcc caggctggag tgcagtggcg ggatctcagt tcactgcaag    900
ctctgcctcc cgggttcacg tcattctcct gcctcagcct cccgatcagc tgggactaca    960
gggcccgcca ccacgcctgg cttatttttt gtatatttat ttatttattt attttaatta   1020 attaatttttt tttttgaga gggagtcttg ctctgtcgcc caggctggaa tgcggtggcg   1080
cgatctcggc tcactgcaag ctccgcctcc caggttcatg ccattctcct gcctcagcct   1140
cctgagtagc tgggactaca ggtacctgcc accatgcccg gctaattttt tgtattttta   1200
gtagacaggg tttcaccttg ttagccagga tggtctcgat ttcctgacct cgtgacccgc   1260
ccgtgttggc ctcccaaagt gctgggatta caggcgtgag ccaccgcgcc cagccatttt   1320
ttgtactttt agtagagacg gggtttcacc gtgttagcaa ggatggtctc aatctcctga   1380
cctcgtgatc tgcccacctg ggcctcccaa agtgctgtga ttacaggcgt aagccaccgc   1440
gcccagcccg tacctttcca ttttctaaaa tatacaaaga atgctggact agaaaccggg   1500
ggacataaaa tttgctatta atcaactgtg tgatcttgga taagtcacct aactttttca   1560
```

| | |
|---|---|
| tagtcaaaaa ctcagtacaa ctgttaagca gtatttgtga attagtgaaa ataagtctac | 1620 |
| tgaacttttg ttgatgttat gttctgccta aatgttaggg agaaaaatca tgattcccca | 1680 |
| actcagaaga atacagtatt ggtagcaaca agtaaagttt gattttttgg tatactttgt | 1740 |
| ggatatatca tagcttttca ttttttgtgga atgataataa aaacacata tgttcagttt | 1800 |
| tgtactgaat cctagcataa tgccaatgaa tggttttttct tcaatgctgg aacagagcca | 1860 |
| tgctgatgaa aaataggata ctaaataagg aaagaattgt taatgtggca gataagcttt | 1920 |
| tgtgttctgg caaaatagag acaattaatg tgtgaatatt ttgtttgctg agtcctatttt | 1980 |
| agatttctaa tatctgtaat atccaaacag aatattttaa ttgtatcaag tcaaaggtta | 2040 |
| aaaaattatg ctattttgct tgtagctaag agtgaaatat tttttcctat atgaaaggca | 2100 |
| tgctacttta ggatagtatt ttatatatat gtatacacac atatacacat atcatttatg | 2160 |
| ttagaactga gaaggacacc aatgatcctg tacttagtaa ttttcaatcc tatctgtata | 2220 |
| ttataaatct gagtaggttt taaaagaaat accaatgcct agttccagcc ctgagattct | 2280 |
| gatgtaattg atatggggttg aggaagggggt gctggacatc agtatatttt caaactttct | 2340 |
| cggataattt attgtgcagc taggatggaa aatcaatgga ctagaggatt tttggtatgc | 2400 |
| tttctagttc taattttctc taattttgaa tagaattcta taggttcctt ctcatcccct | 2460 |
| tttgattcct aaagatacaa agtgatttgt ttgtcattat ataatctatg agacagggtt | 2520 |
| ggaactagaa atttatcctc tgattagcag tccagtgttc tgactgccat attaggctga | 2580 |
| tgattttctt aaggcttgaa acatgcata ttatttaact tattccaagg atgcagttta | 2640 |
| gggtctagat taactatctt ctgatgggag aaacggataa agttaggtta aggccattgg | 2700 |
| aagtcaccgt tttgaatcac acagtagaat ccacaaagtc aagtgaatac aagtctacca | 2760 |
| gtgtaccatc ctaacgtaat ggctttcaac tgtggtcgtg aaaactgacc agatcatggt | 2820 |
| cagtggtggg gttgggtaag tctcaaagag gaaatctatt cactctaagc tggtgatatg | 2880 |
| tttaatattt ttatttcttt cacattttc tctgatgttc acaaggaagg aaatgcactc | 2940 |
| aattgctatt cctgtatcat ttaatccact ctatttgtt tttcagggaa acacctttgt | 3000 |
| ccaagtcccc tatttcccgg accttct | 3027 |

<210> SEQ ID NO 36
<211> LENGTH: 1340
<212> TYPE: DNA
<213> ORGANISM: Artificial
<220> FEATURE:
<223> OTHER INFORMATION: Mus musculus

<400> SEQUENCE: 36

| | |
|---|---|
| aagctgttttt gggcactggt cgtggttgct ggagtcctgt tttgttatgg cttgctagtg | 60 |
| acagtggctc tttgtgttat ctgggtaaga ggagcaacat tgcttttatg taacttctct | 120 |
| gcgcctgccc tctgactata ttaagactct ggcctgtatc ttttctacgt taaagcaaat | 180 |
| gacgcttttc agtctgtcca acttatacat agtaatgatc tgatgtgagt tctgtttccc | 240 |
| agaaggcacc aagtagccag gcagaattag aatgaaatgg gaagattacg gtgggaaatt | 300 |
| agagaattag cttttcttat tcttaatttt ctaacataat aattgcatat caagcagctt | 360 |
| aaatgcatac ataaggtata aaatctaaat ctcatcagga ttaggcaact gaagcccgtg | 420 |
| ctttggcttg gggtcaaaaa tcaggagaaa gtaggctgct gaaattgtgc attcaaacca | 480 |
| gaagaaagca ggtctgttta tgtcagtcct attttctgtc tcttctgaag cagttgccct | 540 |
| gtgtgaggtc aacttggatg ctgtcattat gagactgtaa gaggagaggg actgttcaga | 600 |

```
gctctcccca ctgaatagag attactagtc tctatagatt tttctgcaat aagtttaata     660
gatattttct tcctcaatgt tgaattttg attcaagatt aaacattttg tgttcgtttg     720
attttttttt ttttttttctg agacaatgac tcaccatgtg gaccagattc gtctggaagc    780
tactatgcaa tccaaactga cctcgactca tgtcaatcct cctgcttcat cctcttgagg    840
gcttataggt gtatagcacc atgtctgact tttgaacata tttaaagatt tttgaatttt    900
aatttgtgtg agtaagtgtt ttgcctgcat gcatgtctgt gcaccattta tatgtctggc    960
actcattgaa agccagaaga gggcatcagt ttttctgaaa ctggagttac agatatttgt   1020
gagctaccat gtaggtgctg ggaattgaac cccgttccct ggaagagagg ccagtgctgt   1080
taactgctaa gctatcttcc ttatgcttgt tgaacacatt ttgatgaaca cattcactgt   1140
taagatggta cgaccttaac aaggatcctt tcttagaaa ccctttgtg taggagtaac    1200 agaatgcctt atgtattgat tccaaatgcc tctgattttt ttttccccag aagttgggtg    1260
aatatacagg taagttcttc aatgagaaat gtatgctgca caagacaaaa aagacccctt   1320
atcttgctac tcttcaccca                                              1340

<210> SEQ ID NO 37
<211> LENGTH: 45
<212> TYPE: DNA
<213> ORGANISM: Artificial Sequence
<220> FEATURE:
<223> OTHER INFORMATION: PCR primer

<400> SEQUENCE: 37
ttgtcgtacg ctacaagcat gggcgactgc tttaccaaaa tcttg              45

<210> SEQ ID NO 38
<211> LENGTH: 45
<212> TYPE: DNA
<213> ORGANISM: Artificial Sequence
<220> FEATURE:
<223> OTHER INFORMATION: PCR primer

<400> SEQUENCE: 38
ttttggtaaa gcagtcgccc atgcttgtag cgtacgacaa tgcgg              45

<210> SEQ ID NO 39
<211> LENGTH: 45
<212> TYPE: DNA
<213> ORGANISM: Artificial Sequence
<220> FEATURE:
<223> OTHER INFORMATION: PCR primer

<400> SEQUENCE: 39
cgggcatggt ggcaggtacc tgtagtccca gctactcagg aggct              45

<210> SEQ ID NO 40
<211> LENGTH: 45
<212> TYPE: DNA
<213> ORGANISM: Artificial Sequence
<220> FEATURE:
<223> OTHER INFORMATION: PCR primer

<400> SEQUENCE: 40
cctgagtagc tgggactaca ggtacctgcc accatgcccg gctaa              45

<210> SEQ ID NO 41
<211> LENGTH: 45
<212> TYPE: DNA
```

<213> ORGANISM: Artificial Sequence
<220> FEATURE:
<223> OTHER INFORMATION: PCR primer

<400> SEQUENCE: 41
accagtgccc aaaacagctt agaaggtccg ggaaataggg gactt     45

<210> SEQ ID NO 42
<211> LENGTH: 45
<212> TYPE: DNA
<213> ORGANISM: Artificial Sequence
<220> FEATURE:
<223> OTHER INFORMATION: PCR primer

<400> SEQUENCE: 42
ccctatttcc cggaccttct aagctgtttt gggcactggt cgtgg     45

<210> SEQ ID NO 43
<211> LENGTH: 37
<212> TYPE: DNA
<213> ORGANISM: Artificial Sequence
<220> FEATURE:
<223> OTHER INFORMATION: PCR primer

<400> SEQUENCE: 43
atcgccatgg tgggtgaaga gtagcaagat aaggggt     37

<210> SEQ ID NO 44
<211> LENGTH: 25
<212> TYPE: DNA
<213> ORGANISM: Artificial Sequence
<220> FEATURE:
<223> OTHER INFORMATION: PCR primer

<400> SEQUENCE: 44
ggtagctctt agcatgcttc cccag     25

<210> SEQ ID NO 45
<211> LENGTH: 26
<212> TYPE: DNA
<213> ORGANISM: Artificial Sequence
<220> FEATURE:
<223> OTHER INFORMATION: PCR primer

<400> SEQUENCE: 45
gccagaacac aaaagcttat ctgcca     26

<210> SEQ ID NO 46
<211> LENGTH: 24
<212> TYPE: DNA
<213> ORGANISM: Artificial Sequence
<220> FEATURE:
<223> OTHER INFORMATION: PCR primer

<400> SEQUENCE: 46
gaatgctgga ctagaaaccg gggg     24

<210> SEQ ID NO 47
<211> LENGTH: 25
<212> TYPE: DNA
<213> ORGANISM: Artificial Sequence
<220> FEATURE:
<223> OTHER INFORMATION: PCR primer

<400> SEQUENCE: 47
cttagagcta gagctgccct gtccc     25

```
<210> SEQ ID NO 48
<211> LENGTH: 25
<212> TYPE: DNA
<213> ORGANISM: Artificial Sequence
<220> FEATURE:
<223> OTHER INFORMATION: PCR primer

<400> SEQUENCE: 48
cacgctcctg tcttcccatt cagag                                              25

<210> SEQ ID NO 49
<211> LENGTH: 26
<212> TYPE: DNA
<213> ORGANISM: Artificial Sequence
<220> FEATURE:
<223> OTHER INFORMATION: PCR primer

<400> SEQUENCE: 49
ttggtgcctt ctgggaaaca gaactc                                             26

<210> SEQ ID NO 50
<211> LENGTH: 35
<212> TYPE: DNA
<213> ORGANISM: Artificial Sequence
<220> FEATURE:
<223> OTHER INFORMATION: PCR primer

<400> SEQUENCE: 50
atcgctcgag cggtcagcta tttaggtggt gtagc                                   35

<210> SEQ ID NO 51
<211> LENGTH: 19
<212> TYPE: DNA
<213> ORGANISM: Artificial Sequence
<220> FEATURE:
<223> OTHER INFORMATION: sgRNA sequence

<400> SEQUENCE: 51
tagggcgtga acagcgacg                                                     19

<210> SEQ ID NO 52
<211> LENGTH: 19
<212> TYPE: DNA
<213> ORGANISM: Artificial Sequence
<220> FEATURE:
<223> OTHER INFORMATION: sgRNA sequence

<400> SEQUENCE: 52
aaaccgtcgc tgttcacgc                                                     19

<210> SEQ ID NO 53
<211> LENGTH: 22
<212> TYPE: DNA
<213> ORGANISM: Artificial Sequence
<220> FEATURE:
<223> OTHER INFORMATION: sgRNA sequence

<400> SEQUENCE: 53
taggtcatct cctaagctgt tt                                                 22

<210> SEQ ID NO 54
<211> LENGTH: 22
<212> TYPE: DNA
<213> ORGANISM: Artificial Sequence
<220> FEATURE:
```

```
<223> OTHER INFORMATION: sgRNA sequence

<400> SEQUENCE: 54
aaacaaacag cttaggagat ga                                                22
```